(12) United States Patent
Shao et al.

(10) Patent No.: US 6,709,850 B2
(45) Date of Patent: Mar. 23, 2004

(54) ISOLATED HUMAN ENZYME PROTEINS, NUCLEIC ACID MOLECULES ENCODING HUMAN ENZYME PROTEINS, AND USES THEREOF

(75) Inventors: Wei Shao, Frederick, MD (US); Gennady V. Merkulov, Baltimore, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 156 days.

(21) Appl. No.: 10/109,856

(22) Filed: Apr. 1, 2002

(65) Prior Publication Data

US 2003/0166185 A1 Sep. 4, 2003

Related U.S. Application Data

(62) Division of application No. 09/820,005, filed on Mar. 29, 2001, now Pat. No. 6,489,149.

(51) Int. Cl.$^7$ .......................... C12N 9/04; C12N 15/00; C12N 5/00; C07K 1/00; C07H 21/04
(52) U.S. Cl. .................... 435/190; 530/350; 435/320.1; 435/325; 435/252.3; 435/6
(58) Field of Search .............................. 435/190, 320.1, 435/325, 6, 252.3; 530/350

(56) References Cited

PUBLICATIONS

Rodaway et al., Mol. Cell. Biol., 10(9), 5388–5396, 1990, see the attached sequence alignment.*

* cited by examiner

*Primary Examiner*—Maryam Monshipouri
(74) *Attorney, Agent, or Firm*—Celera Genomics; Justin D. Karjala

(57) ABSTRACT

The present invention provides amino acid sequences of peptides that are encoded by genes within the human genome, the enzyme peptides of the present invention. The present invention specifically provides isolated peptide and nucleic acid molecules, methods of identifying orthologs and paralogs of the enzyme peptides, and methods of identifying modulators of the enzyme peptides.

4 Claims, 19 Drawing Sheets

```
  1 CCTGGAAGTG CCAGGGAGCA CTGGAGGCCA CCCAGTCATG GGGGACACCT
 51 TCATCCGTCA CATCGCCCTG CTGGGCTTTG AGAAGCGCTT CGTACCCAGC
101 CAGCACTATG TGTACATGTT CCTGGTGAAA TGGCAGGACC TGTCGGAGAA
151 GGTGGTCTAC CGGCGCTTCA CCGAGATCTA CGAGTTCCAT AAAACCTTAA
201 AAGAAATGTT CCCTATTGAG GCAGGGGCGA TCAATCCAGA GAACAGGATC
251 ATCCCCCACC TCCCAGCTCC CAAGTGGTTT GACGGGCAGC GGGCCGCCGA
301 GAACCGCCAG GGCACACTTA CCGAGTACTG CAGCACGCTC ATGAGCCTGC
351 CCACCAAGAT CTCCCGCTGT CCCCACCTCC TCGACTTCTT CAAGGTGCGC
401 CCTGATGACC TCAAGCTCCC CACGGACAAC CAGACAAAAA AGCCAGAGAC
451 ATACTTGATG CCCAAAGATG GCAAGAGTAC CGCGACAGAC ATCACCGGCC
501 CCATCATCCT GCAGACGTAC CGCGCCATTG CCAACTACGA GAAGACCTCG
551 GGCTCCGAGA TGGCTCTGTC CACGGGGGAC GTGGTGGAGG TCGTAGAGAA
601 GAGCGAGAGC GGTTGGTGGT TCTGTCAGAT GAAAGCAAAG CGAGGCTGGA
651 TCCCAGCGTC CTTCCTCGAG CCCCTGGACA GTCCTGACGA GACGGAAGAC
701 CCTGAGCCCA ACTATGCAGG TGAGCCATAC GTCGCCATCA AGGCCTACAC
751 TGCTGTGGAG GGGGACGAGG TGTCCCTGCT CGAGGGTGAA GCTGTTGAGG
801 TCATTCACAA GCTCCTGGAC GGCTGGAAAG ACGACGTCAC AGGCTACTTC
851 CCGTCCATGT ACCTGCAAAA GTCAGGGCAA GACGTGTCCC AGGCCCAACG
901 CCAGATCAAG CGGGGGGCGC CGCCCCGCAG GTCGTCCATC CGCAACGCGC
951 ACAGCATCCA CCAGCGGTCG CGGAAGCGCC TCAGCCAGGA CGCCTATCGC
1001 CGCAACAGCG TCCGTTTTCT GCAGCAGCGA CGCCGCCAGG CGCGGCCGGG
1051 ACCGCAGAGC CCCGGGAGCC CGCTCGAGGA GGAGCGGCAG ACGCAGCGCT
1101 CTAAACCGCA GCCGGCGGTG CCCCCGCGGC CGAGCGCCGA CCTCATCCTG
1151 AACCGCTGCA GCGAGAGCAC CAAGCGGAAG CTGGCGTCTG CCGTCTGAGG
1201 CTGGAGCGCA GTCCCCAGCT AGCGTCTCGG CCCTTGCCGC CCCGTGCCTG
1251 TATATACGTG TTCTATAGAG CCTGGCGTCT GGACGCCGAG GGCAGCCCCG
1301 ACCCCTGTCC AGCGCGGCTC CCGCCACCCT CAATAAATGT TGCTTGGAGT
1351 GGAAAAAAAA AAAAAAAAAA AAAAAAAAAA AA
     (SEQ ID NO: 1)
```

FEATURES:
5'UTR:          1 - 37
Start Codon:    38
Stop Codon:     1196
3'UTR:          1199

Homologous proteins:
Top 10 BLAST Hits:

| Sequences producing significant alignments: | Score (bits) | E Value |
|---|---|---|
| CRA\|18000004925255 /altid=gi\|4557785 /def=ref\|NP_000256.1\| neut... | 789 | 0.0 |
| CRA\|18000005124568 /altid=gi\|2754713 /def=gb\|AAB95193.1\| (U5783... | 788 | 0.0 |
| CRA\|18000005207006 /altid=gi\|4263750 /def=gb\|AAD15422.1\| (AC004... | 783 | 0.0 |
| CRA\|18000005171728 /altid=gi\|6685673 /def=sp\|O77774\|NCF1_BOVIN ... | 684 | 0.0 |
| CRA\|148000004473069 /altid=gi\|8439513 /def=dbj\|BAA96544.1\| (AB0... | 670 | 0.0 |
| CRA\|118000005118410 /altid=gi\|9623382 /def=gb\|AAF90134.1\|AF2677... | 663 | 0.0 |
| CRA\|18000005141875 /altid=gi\|3061282 /def=dbj\|BAA25649.1\| (AB00... | 659 | 0.0 |
| CRA\|18000005020732 /altid=gi\|1171669 /def=sp\|Q09014\|NCF1_MOUSE ... | 655 | 0.0 |
| CRA\|18000004937799 /altid=gi\|2118398 /def=pir\|\|I54525 leukemia-... | 651 | 0.0 |
| CRA\|148000001425618 /altid=gi\|7839599 /def=gb\|AAF70344.1\| (AF26... | 527 | e-148 |

EST:

| Sequences producing significant alignments: | Score (bits) | E Value |
|---|---|---|
| gi\|12896059 /dataset=dbest /taxon=960... | 1532 | 0.0 |
| gi\|12951967 /dataset=dbest /taxon=960... | 1501 | 0.0 |
| gi\|12342004 /dataset=dbest /taxon=96... | 1423 | 0.0 |

EXPRESSION INFORMATION FOR MODULATORY USE:
gi|12896059 placenta
gi|12951967 B cells from Burkitt lymphoma
gi|12342004 primary B-cells from tonsils Tissue Expression:
Leukocyte

FIGURE 1

```
  1 MGDTFIRHIA LLGFEKRFVP SQHYVYMFLV KWQDLSEKVV YRRFTEIYEF
 51 HKTLKEMFPI EAGAINPENR IIPHLPAPKW FDGQRAAENR QGTLTEYCST
101 LMSLPTKISR CPHLLDFFKV RPDDLKLPTD NQTKKPETYL MPKDGKSTAT
151 DITGPIILQT YRAIANYEKT SGSEMALSTG DVVEVVEKSE SGWWFCQMKA
201 KRGWIPASFL EPLDSPDETE DPEPNYAGEP YVAIKAYTAV EGDEVSLLEG
251 EAVEVIHKLL DGWKDDVTGY FPSMYLQKSG QDVSQAQRQI KRGAPPRRSS
301 IRNAHSIHQR SRKRLSQDAY RRNSVRFLQQ RRRQARPGPQ SPGSPLEEER
351 QTQRSKPQPA VPPRPSADLI LNRCSESTKR KLASAV
(SEQ ID NO: 2)
```

FEATURES:
Functional domains and key regions:
[1] PDOC00001 PS00001 ASN_GLYCOSYLATION
N-glycosylation site

```
        131-134 NQTK
```
---
[2] PDOC00004 PS00004 CAMP_PHOSPHO_SITE
cAMP- and cGMP-dependent protein kinase phosphorylation site Number of matches: 4
```
    1     42-45  RRFT
    2    297-300 RRSS
    3    313-316 KRLS
    4    321-324 RRNS
```
---
[3] PDOC00005 PS00005 PKC_PHOSPHO_SITE
Protein kinase C phosphorylation site Number of matches: 10
```
    1     36-38  SEK
    2     53-55  TLK
    3    133-135 TKK
    4    160-162 TYR
    5    300-302 SIR
    6    311-313 SRK
    7    324-326 SVR
    8    352-354 TQR
    9    377-379 STK
   10    378-380 TKR
```
---
[4] PDOC00006 PS00006 CK2_PHOSPHO_SITE
Casein kinase II phosphorylation site Number of matches: 11
```
    1     53-56  TLKE
    2     93-96  TLTE
    3    148-151 TATD
    4    171-174 SGSE
    5    178-181 STGD
    6    208-211 SFLE
    7    215-218 SPDE
    8    238-241 TAVE
    9    246-249 SLLE
   10    279-282 SGQD
   11    344-347 SPLE
```
---

FIGURE 2A

[5] PDOC00008 PS00008 MYRISTYL
N-myristoylation site

Number of matches: 3
   1     83-88    GQRAAE
   2    172-177   GSEMAL
   3    280-285   GQDVSQ Membrane spanning structure and domains:
   NO DATA BLAST Alignment to Top Hit:
>CRA|18000004925255 /altid=gi|4557785 /def=ref|NP_000256.1| neutrophil
         cytosolic factor 1; Neutrophil cytosolic factor-1 (47kD);
         p47phox [Homo sapiens] /org=Homo sapiens /taxon=9606
         /dataset=nraa /length=390
         Length = 390

Score =  789 bits (2015), Expect = 0.0
 Identities = 385/390 (98%), Positives = 386/390 (98%), Gaps = 4/390 (1%)
 Frame = +2

Query: 38    MGDTFIRHIALLGFEKRFVPSQHYVYMFLVKWQDLSEKVVYRRFTEIYEFHKTLKEMFPI  217
             MGDTFIRHIALLGFEKRFVPSQHYVYMFLVKWQDLSEKVVYRRFTEIYEFHKTLKEMFPI
Sbjct: 1     MGDTFIRHIALLGFEKRFVPSQHYVYMFLVKWQDLSEKVVYRRFTEIYEFHKTLKEMFPI  60

Query: 218   EAGAINPENRIIPHLPAPKWFDGQRAAENRQGTLTEYCSTLMSLPTKISRCPHLLDFFKV  397
             EAGAINPENRIIPHLPAPKWFDGQRAAENRQGTLTEYCSTLMSLPTKISRCPHLLDFFKV
Sbjct: 61    EAGAINPENRIIPHLPAPKWFDGQRAAENRQGTLTEYCSTLMSLPTKISRCPHLLDFFKV  120

Query: 398   RPDDLKLPTDNQTKKPETYLMPKDGKSTATDITGPIILQTYRAIANYEKTSGSEMALSTG  577
             RPDDLKLPTDNQTKKPETYLMPKDGKSTATDITGPIILQTYRAIA+YEKTSGSEMALSTG
Sbjct: 121   RPDDLKLPTDNQTKKPETYLMPKDGKSTATDITGPIILQTYRAIADYEKTSGSEMALSTG  180

Query: 578   DVVEVVEKSESGWWFCQMKAKRGWIPASFLEPLDSPDETEDPEPNYAGEPYVAIKAYTAV  757
             DVVEVVEKSESGWWFCQMKAKRGWIPASFLEPLDSPDETEDPEPNYAGEPYVAIKAYTAV
Sbjct: 181   DVVEVVEKSESGWWFCQMKAKRGWIPASFLEPLDSPDETEDPEPNYAGEPYVAIKAYTAV  240

Query: 758   EGDEVSLLEGEAVEVIHKLLDGW----KDDVTGYFPSMYLQKSGQDVSQAQRQIKRGAPP  925
             EGDEVSLLEGEAVEVIHKLLDGW    KDDVTGYFPSMYLQKSGQDVSQAQRQIKRGAPP
Sbjct: 241   EGDEVSLLEGEAVEVIHKLLDGWWVIRKDDVTGYFPSMYLQKSGQDVSQAQRQIKRGAPP  300

Query: 926   RRSSIRNAHSIHQRSRKRLSQDAYRRNSVRFLQQRRRQARPGPQSPGSPLEEERQTQRSK  1105
             RRSSIRNAHSIHQRSRKRLSQDAYRRNSVRFLQQRRRQARPGPQSPGSPLEEERQTQRSK
Sbjct: 301   RRSSIRNAHSIHQRSRKRLSQDAYRRNSVRFLQQRRRQARPGPQSPGSPLEEERQTQRSK  360

Query: 1106  PQPAVPPRPSADLILNRCSESTKRKLASAV  1195
             PQPAVPPRPSADLILNRCSESTKRKLASAV
Sbjct: 361   PQPAVPPRPSADLILNRCSESTKRKLASAV  390  (SEQ ID NO: 4)

FIGURE 2B

Hmmer search results (Pfam):
HMM results:

Scores for sequence family classification (score includes all domains):

| Model | Description | Score | E-value | N |
|---|---|---|---|---|
| CE00053 | CE00053 mox_mitogenic_oxidase | 573.6 | 1.3e-168 | 1 |
| PF00787 | PX domain | 119.4 | 6.6e-32 | 1 |
| PF00018 | SH3 domain | 107.5 | 2.7e-28 | 2 |
| CE00036 | CE00036 androstane_receptor | 0.3 | 4.6 | 1 |

Parsed for domains:

| Model | Domain | seq-f | seq-t | hmm-f | hmm-t | score | E-value |
|---|---|---|---|---|---|---|---|
| PF00787 | 1/1 | 4 | 121 .. | 1 | 147 [] | 119.4 | 6.6e-32 |
| PF00018 | 1/2 | 159 | 213 .. | 1 | 57 [] | 66.7 | 1e-16 |
| CE00036 | 1/1 | 243 | 257 .. | 199 | 213 .. | 0.3 | 4.6 |
| PF00018 | 2/2 | 229 | 279 .. | 1 | 57 [] | 41.0 | 1.2e-09 |
| CE00053 | 1/1 | 1 | 386 [] | 1 | 566 [] | 573.6 | 1.3e-168 |

FIGURE 2C

```
   1 TACTAAAAAT ACAAAATTAG CCAGGCGTGG TGGCGCACAC CTGTAATCCC
  51 AGCTACTTGG GAAGCTGAGG CAGGAGAATC GCTTGAACCT GGAAGGCAGA
 101 GGTTGCAGTG AGCCGAGATT GTGCCACTGC ACTCCAGCCT GGGCAACAAG
 151 AGCGAAACTT CGCTTCAAAC AAATAAATTA ACGCCCAGCA TGTCTTGGCT
 201 TTCATCTGCC AGACCTCAAC CCTCACCCCC AGGAGATCAG GTCCGGACCA
 251 TGAGCTGACC CTGGACTCAG GCAAGGGTGA GTTGGTGCAG CCCTGGCCTG
 301 CTGGGAGGCA CAGGCTGCAG CAGGCTGCCT GGGGCTGAGG CCCGCCACTC
 351 ATGAACTCAT GACCTTGAAT GAGCTCCAAA AGCTCTGGGC CTCCCAGGCT
 401 CTAGGGGGAG TGGGAGAGAG AGGCCTCAGC CTGTCCCTGG GCATGCTGCC
 451 CCCTCCTCAC CTCTTTGTCC CAAATCCCCT TCCTGGCAAA GCTGACAGTC
 501 TTAATATCAC TCTGGAGAAA ACTGAGTCAG CCCTAAGGAA CAATTCAATG
 551 AACCATTTGC TTACTTGAGG ATTGGAACTC AAGTCTCACT CAAAGTCTGT
 601 GCCATTTTCG TCCCAGCTGT CACTGGCCCT CATCCACACA CACCCAAGGA
 651 TGAGCATCTA ACGCTTGCAT GCACACTCCC ATGCCCGCGT TCATTCACTC
 701 ATTCATTCAT TCATTCACTC ATTCATTGAC TCATTCATTC ATTCACTCAC
 751 TCATTCATTC ACTCAGTGAA TGTTGCAGTC ACGATCCAAA TATTTATGGC
 801 CTCTGTGTGC CAGGCACTAG ATGGAGGGGC TGGGGCTAGA GCCCCTGATA
 851 ACCCGGTCAT GCCCTAGCTT TCCTGGGACA CACATTGTGG TAAGGGGAGA
 901 CTAAAAAAAT TAAGTCAGGC CAGGCACGGT GGCTCATGCC TGAATCCCAG
 951 CACTTTGGGA GGCCGAGGCG AGTGAATTAC CTGAGGTCAG GAGTTCAAGA
1001 CCAGCCTGGC CAACATGGAG AAACCCAGTC TCTAATTAAA AAAAAAAAA
1051 AAATTAGCCA GGTGTGGTGG CACATGCCTG TAATCCCAGC TACTCAGGAG
1101 ACTAACGCAA GAGAATTGCT TGAACCCAGG AGGCAGAGGT TGCGGTGAGC
1151 CGAGATCGCG CCATTGCACT CCAGCCTGGG AAACAAGAGC GAGACTCCAT
1201 CTCAAAAAAA AAAAAAGTGG GAGGCAGAGG CAGGAGGATC ACTAGAGGCC
1251 AGTAGTTTGA GACCATCCTG GGCAACAGTA CAGGACCCTG TCTGTACAAA
1301 AAAATTAAAA AAAATTTAAC CGGGCATGGT GGCACACACC CGTAGTCCCA
1351 GCTACTCCAG AGGCTGAGGC AGGAGGATCG CTGGAGCCCA GGAGTTGGAG
1401 GCTGCAGTGA ACTGTGATCC CACCACTGCA CTTAAGCCTG GATAACAAAG
1451 CAAGACCCTG TCTCAAATAA CAATAGCAAT AATAATAAAG AAAAATTAAA
1501 TGCAATTTGC GATGCATCAG TGATAAGTGC TCTGCAGAAA AAGGAGGCAG
1551 GAAGAGGCTG AGAAAGGTAT GAGGTTTGCT ATGCAATGTG AAGTTATCAA
1601 GGAAGGCTTC TCGGAAGAGG TGACATTTGA GCAGAGAAAT GGAGGAGAGT
1651 TATGGAGGGA AGATGGTGAA TGGGGGGAAC ATGGTCAAGA CCAGGAATAT
1701 GGTCAAGGGG GGAAAGATGG TCAAGGGGAC GCAGCAAATG CAAAGGCCCT
1751 GAGGCAGGAG CAGCTTGATT CACCCCCAAA ACCCGTGGGG CCCGTGCAGG
1801 CGACGGGAAG GACAAGTGTA AACCCTTTTC CTTGTCCCTG CAGGTGTGTG
1851 TGAACATGAG TCTGCCCATG TTTACACCCT GCAAGCCTGA AGAGTCCCCA
1901 GAAACTGAAA GAAGAAGCAA AGCCCTTTCT GTACCCTCCC TGCCCCCTGT
1951 CCCGACCGCG ACAAAAGCGA CTTCCTCTTT CCAGTGCATT TAAGGCGCAG
2001 CCTGGAAGTG CCAGGGAGCA CTGGAGGCCA CCCAGTCATG GGGGACACCT
2051 TCATCCGTCA CATCGCCCTG CTGGGCTTTG AGAAGCGCTT CGTACCCAGC
2101 CAGCACTATG TGAGTAGCTG GTGGAGGGCA TCCCGTGGGG GGAATACGGG
2151 AGGGACAGCA CGGCCACCCT TGCAGTCCCA GGGCCAACCA GCTCCAGTGA
2201 GGACTAACGG GGCAGGGTCT TGGGCACCTG GTCCCTGGTC TTTGAGCCTG
2251 GATCTACCCC TCTGATCCCT GGGAAGACAG TTCCCTTGGA CCCGCCCTGG
2301 GCCCCAGCCC TTTACTGTCC CCGCCTGTGT CCCCAGCCAG GCCCTCAGCC
2351 TTAGCCAGGA GTCCTCTTTC TGCTCCCCTG CCATGGCCAG GCAGCCCAGC
2401 GCTCTCTCAG GTCCGAGGCC CACTCCTCCA GGAAGCCTTC CCTGACTAGC
2451 CCAGCTATCA GAGAGTGGCC CTCCCAAGAG GGAGGCCTGG AAACTAAAGC
2501 TCTCTCTCTC CCCAGCTGCC TGTAGTGTCA GTTAGAGTCT TATCCTCTCC
2551 AGTAGGGTGA CACCATGACA GGGGCCAATA GAGTCCTCCC ATCTGTCCCC
2601 AAGGAGGCTG GACAAATGCC TGCTCAGACA CACAAGTCCA CTGGGTCCCC
2651 TAATCCCATA GGAAGGCCAG GGAGGAACTA CATTTAGGAA ATTGAAGCTT
2701 GTATGGAACA TTTAGTCCTA TGTGCCAAGA CCTTTCTCTT TTTTGTTATT
2751 TTTTTGTGTT TTGAGACAGA GTCTTGATCT GTTGCCCAGG CCAGAGTGCA
2801 GTGGCACGAT CTCAGCTCAC TGCAACCTCC GCCTTCCAGG TTCAACTGGT
2851 TCTCCTGCCT CAGCCTCCAG AGTAGTTGGG ATTACAGGTG CCCACCACCA
2901 CGCCTGGCTA ATTTTTGTAT TTTTAGTAGA GACAGGGTTT CACCATGTTG
2951 GCCAGACTGG TCTCAAACTC CTGACCTCAA GTGATCCACC CACCTGGGCC
3001 TCCCAAAGTG CTGGGATTAC AGGCATGAGC CACCGTGCCT GGCCTGTTTT
3051 TTTGAAATGA GGTCTGGAGT GCAGTGGTGC GATCATAGTT CACTGCAGCC
3101 TCAACCTCCC AGGCCCAAGT GATCCTCCTG CCTCAGCCCC TTGAGTGCT
3151 GGGCTACAG GCGCACACCA CCATGCCTGG CTAGTTTTTA AAATTTTTGT
3201 GGAGATGAGG TTTCACTATG TTGTCCAGGC TAATCTTGAA CTCCTCGGCT
```

FIGURE 3A

```
3251 TAAGCAACCC TCTGGTCTCA GCCTCCCACA GTGCTAGGAT TACAAGCGTG
3301 AGCTACCGTG CCTAGTCACT TTTCTCCTTT TCTTTGTAAC TTTCAGTTTT
3351 GAAATTTCAA ATTTACAGAA AGGCTACTGG GTGTCAAAAC GGTACCAGTC
3401 ACTCCAATAG TCTTTCACTC ACCTTCATCC ACACCTCTCT TTCTGGGGAT
3451 ATTTTCTGAA TTATTTGAGA GTGAGTTGAA GACGTGTTTC TTTACCTCTA
3501 AATACTAGTT GTTGGGCATT TCTTAAAATC AAGGCATTCT CTTACATAAT
3551 CACAACACAC GTGTCAAAAT CAGGAAATTA ACATGGACAA AACACCATTA
3601 TCCACCCACA GACTTTACTG AGGTTTCCCC GATTATCCTG CTTGTCCTCT
3651 GCAGTGAAAA CTTTTTTCAG GTCTAGGATC CAGTCAAGGA TCAATGTCAT
3701 AGCCTTTAAC CTTCTTTAAT CTGGATCAGT CTTTTTTCTT TTTCTTTTTC
3751 TTTTTTTGGA CACGGAATCT CACTCTGTCG CCAGACTGGA GTGCAGTGGT
3801 GCAATCTCGG CTCATTGCAA CCTCTGCCTC CTGGGTTCAA GAGATTCTCC
3851 TGCCTCAGCC TCCTGAGTAG CTGGGAATAC AGGTGCGCGC CACCACGCCC
3901 AGCTCGTTTT TGGTAGAGAC AGGGTTTTGC CATTGATTCT GGATCAGTCT
3951 TTTTTTTTTT TTTTATGAGA TGGAGTCTTA CTCTGTCACC CAGGCTGGAG
4001 TGCAATGGCA CAATCTCCAC TCACTGCATC CTCCGCCTCC CAGGTTCAAG
4051 CAATTCTCGT GCCTCAGCCT CCCGAGTAGC TGGGATTACA GGCATGCGCC
4101 ACCATGCCCG GCTACTTTTT GTATTTTTAG TAGAGACAGG GTTTCACCAT
4151 GTTAGCCAGG CTGATCTCGA ACTCCTGACG TCAGGTGATC TGCCCGCCTC
4201 GACCTCCCAA AGTGCTGGGA TTACAGGCGT GAGCCACCGT GCCAGCGGAT
4251 TCTGGATCGG TCTTAATCAG TCTTTGTCTT TTGCAACTTT GATGTTTTGC
4301 AGAGAGCAGA CCAGTTACCT TGTAGAATGT CCCTTAGTTT GGGTTTATCT
4351 TCATTAGATT CAGTTTGTGT ATCCAGGGCA GTGGATCTTA GATGCAATTC
4401 TGTCTTCTTT TTAATTTTTT TGAGAGGGAG TCTCGCTCTG TCACCCAGGC
4451 TGGAGTGCAG TGGCACAACC TCAGCTCACT GCAGCCTCCG CCTCCCGGGT
4501 TCAAGCAATT CTCCTGTCCC AGCCTCCCAA GTAGCTGGGA TCACAGGTGC
4551 CCATCACCAC TACCGGGTAA TTTTTGTGTT TTTAGTAGAG ACAGGGTTTC
4601 ACCATATTGG TCAGGCTGGT CTTGAACGCC TGACCTCAGG TGATCCACCT
4651 GCCTTGGCCT CCCAAAGTGC TGGGATTACA GACGGGAGCC AACATGCCCA
4701 GCCTTCCTGC CCCTCCCGTC CCCTCCCCTC TCCTCCTGTC CCCTCCCTTC
4751 CCCTCCCCTA TCCTCATGTC CCCTCCCTTC CCCTCCCCTC CCCACCCAAG
4801 CTGGAGTGCA GTGGTGCAAT CATAGCTCAC TAAAGCCTTG ACCTCCAAGT
4851 CTCAAGCAAT TCTCCTGCCT CACCTGGGGC CACAGGTGTG CGGCACCACA
4901 CCCGGACAAT TTTTGTGTTT TTAGTAGATA TGGGGGTCTC GCTATGTTGC
4951 CCAGGCTGGT CTCAAACTCT TGGACTCAAG CGATCTTCCC ACCTCGGTAC
5001 TAAAAAGTGC TGGGATTCCA GGTGTGAGCC ACCGTGCCCA GCCTAGGTCC
5051 TACTTTTATC TCCAATTTAC AGATGAGTCC ATTTGAGAGA AGCTGACCCT
5101 CTTGCCCTGG GTCTCAAGGC TGGGGCGTGG CAGCACTTGG GTCCACGTTT
5151 GTGCCCTTTC TGCAATCCAG GACAACTGCA AAGATGGTCC TCACCCCAAT
5201 CCTCTGGGCT TCCTCCAGTG GGTAGTGGGA TCCTGGGTGC ACACAGCAAA
5251 GCCTCTTTGG AGGCTGAATG GGGTCCCCCG ACTCTGGCTT TCCCCCAGGT
5301 ACATGTTCCT GGTGAAATGG CAGGACCTGT CGGAGAAGGT GGTCTACCGG
5351 CGCTTCACCG AGATCTACGA GTTCCATGTG AGTGTGGGGA CGGAGGAGGG
5401 ACAGGGACCC ACCGTTCCAG CTCCACCCTT TGGGAAGGAC CTTAGCCCAG
5451 GTGATGGGGA AACTGCAGAA CCCAGAATCC CCTCCCAGAC CACAGTTAAA
5501 GGGGATTTAT TTATTTATAT AAATTTTTGT GACAGGGTCT TGCTCTGTCA
5551 CCCAGGGTCT TGCTCTGTCA CCACTCTGAA CACCTCATGT TCTCTGATTA
5601 CAGGCATGAG CCCCCACGGT CGGCCTTTTA GGTGGTTTTG AGAGGTATTT
5651 AGGTTTGCAG TGCAGGGGCG CAATCATAGC TCACTGCAGC CTCAACCTCT
5701 GGGGCTCAAG CGATCCTCCT GCCTCAGCCT CCTGAGTAGC TGGGACTATA
5751 GGTGCGCATC ACCATGTGTG GCTAATTTTT GTATTTTTTA TAAAGATGGG
5801 GATCTCACTA TGTTGCCCAG GCTGGTCTTG AACTCCAGAC CTCAAGTGAT
5851 CCTCCTGCCT TGGCCTCCCA AAGCTAAGGG GGCATTAAAA GAAAAAAACA
5901 TTTTTCCCCC TGAAACATTT AAGTAGTCTT ACTGAAAACA ATAAAACACA
5951 GAAACACCAG ATTCTCATTT TAAAGTAAAA CAGACAGGAT CTCCCAGAAC
6001 CTTCCTAGAA TGGAACCATT CTTGTCGCTT TTGAAAAACA AAGCCAAGTT
6051 CTAGATCCCA AATAAATGCA CCTGCTGGTG AACATTCTCC TTGTGGTTCT
6101 CGTCCCTATG TTAGTTATTT TCCTAAATTT TACATTTGTA CCTTTTTAAG
6151 AATGAGTTAT CAGTTTTTTT ATATTTGCTT TTCTTTTGAG ATGGGGTCTT
6201 GCTCTGTCAC CCAGGCTGGG GTGCAGTGGT GCAATCACGG CTCACTGCAG
6251 CCTCAACCTC CAGGGCTGAA GCGATTCTCC CATCTCAGCC TCCCATGTTG
6301 AGATCACAGG TGTGCACCAC CACACCTGGC TCCTTTTCCT GATTTGTTTT
6351 TTGTAGAGAT GGGATTTCGC TATGTTGCCC AGGCTGGTCT CTAACTCCTG
6401 GACTCAAGTG ATCCTCCCGC CTCAGCTTCC CAAATTGCTA GGATTACAGG
6451 TTTGAGCCCC TGCACCTGGT CAACCTGAGT TTTAAGAGGA TCCCTTTGGC
```

FIGURE 3B

```
6501 GACTGGATTG AGGACAGACA AGAGTGGACG GGGGACACAA GGAGGCCATT
6551 TTCGTTATCC AGGCCTGGTA GTGGCTAGGG CCAGGAGGGT GGGGTTGGTG
6601 GGAAGCAGTC AGATCCCAAA GAGATTTGGG GATTGGAAGC AAAAGGATTT
6651 GCTGGTGACT TGCACATGGG AGGGAGAGAG GTCAGTGCCT CTGTTAATCA
6701 AGGAATCCAG ATTGCCACCG AAATTTCTAG GCCCGAGATA TTTAGGTAGT
6751 GTCTCACTCT GTCACCCAGG ATGGAGTGCA GTGGCGCCAT CTCGGCTCAC
6801 TGTAACCTCC GCCTCCCAGG TTTAAACGAT TCTCCCACCT CAGCCTCCTG
6851 AGTAGCTGGG ATTACAGGCA TGTGCCACCA CTCCCGGCTA ATTTTTGTAT
6901 TTTTAGTAGA GACGGGGTTT CACCACGTTG GCCAGGCTGG TCTTGAACTC
6951 CTGACCTCAA GTGATCCACC CACGACAGCC TCCCAAAGTG CTGGGATTAC
7001 AGGCGTGAGC CACCATGCTC GGCCTTTTAG GTGGTTTTGA GAGGTATTTA
7051 GGTCACTTCC AATCTCGTGC TTTTCCAAGT GTTGTAAACT ACAAATATTC
7101 CTTCACGTCT TCTTGTCTTT TTAATGTTTA GAAAACCTTA AAAGAAATGT
7151 TCCCTATTGA GGCAGGGGCG ATCAATCCAG AGAACAGGAT CATCCCCCAC
7201 CTCCCAGGTG AGCACGGGGC TGAGCCGCCT GTCAGGGGGT CATTGGCGGG
7251 GGCTCACCTG CCCTCCCAGC ACCTCTCGGG CTTGACCTCA TGTTCTCTGG
7301 TGCCAGCTCC CAAGTGGTTT GACGGGCAGC GGGCCGCCGA GAACCACCAG
7351 GGCACACTTA CCGAGTACTG CAGCACGCTC ATGAGCCTGC CCACCAAGAT
7401 CTCCCGCTGT CCCCACCTCC TTGACTTCTT CAAGGTGCGC CCTGATGACC
7451 TCAAGCTCCC CACGGACAAC CAGTGAGTGA ACTTTTCACC CTGCCAGGTG
7501 GGAGAGGGAA GGAGGGGTGG GACTTTCTGT GTTTTGCAGA TGAGGAAACC
7551 AAGGCTCAGA GAGGGAAAGC CACCTTCCCA GAGCCACACA GCCAGAAAGA
7601 GGAGGCAAAT TCCACCTCCG GCCCCTGTGA CCCCGCCAAG CCTCCACCTT
7651 AATCTTTCAC ACCTCAGGGC ACTGGGGGAA GCACTCGGGG CTGGAGGTTC
7701 AAAGTCCTGG GTCCTCATCC TGACATTATG GCCACCTGGC CATGGGACCT
7751 GGAGCCAGTC ACCACTGCTC TCTGAATGCA GGTTCTCCAT TTCTATAATG
7801 GGCAGTGAGG ATCAGATGAA GCATTGGGTG TCTTGCGGAG CCCCCCAGAA
7851 GGATGTGGGG TTGATGCCTC TGCTAAGTGC TGAGCATGTC TGGGGTCTCC
7901 TGTACCCAGG ACCCTGTGTG AAGGCACCT GAGAGGCTGA GGGAGCTCCA
7951 GGCAGGCTGG GGAAGTCCCC TTCTCCACTC CTCTCTGGTC ACTGAAGCTC
8001 GAAGTGGGGA GCATGAGGAC AGGACGTTAC CCCTTGTCAA GGCACCCAGG
8051 CTGCCAAGAC AGAGACAAGC AGCATTGCTC CGGCCAGCAC TTATTGACGC
8101 TTGAAGGTGT CCCCTGGCCC AAGGAAGGGC AGTTATCATC AGCCCGGGAG
8151 GCGGGGGAAG GATGACTCT GCAGTGGGGT CCGCTCCTCA TTGCCTGCTC
8201 TCTCAGGGCT CCAGAAGGAG GAAGAGGCCG GGCACAGTGG CTCACACCTA
8251 TAATCCCAGC ACTTTGGAAG GTCGAGGTGG GCAGATCACC TGAGGTTGGG
8301 AGTTTGAGAC CAGCCTGGCC AACATGGTGA AACCCCATCT CTACCAAAAA
8351 TATAAAAATT TAGTCAGGCA TGGTGGTGTG CGCTTGTAAT CCCAGCTACT
8401 TGGGAGGCCG AGGCAGGAGA ATCGCTTGAA CCCGGGAGGC AGAGGTTGCA
8451 GTGAGCTGAG ACTGCGCCAC TGCACTCCAG CCTGGGTGAC AGAGCGAGAC
8501 TCTGTCTAAG AAAAAAAAAA GAAAAGAAGA AAGAAGATGG CCTGGGAGCC
8551 CGCAAGAGCA TTTTCCAGGC TTAGGGCATC CTTTGGGTCT GCAGAAGGCT
8601 ATGCAGTGTC CTCCTCATGT CCCTCCCTTG GGCTGCCCGA GACGATCCGC
8651 CCGCCCCCAT CACTTCCTGA AGCCCTTCCT CAGCCAGTCC AGTTGCTGTC
8701 TTCTCTCCGC AGTGCCCCTT CCCTTTCCCG GGTCCCTCTT CTCTTGGGAA
8751 GTTCTTCTGC AGGTCTACCC AGTGCCTCTT CTTCCTCCAT GGGAAGCCAA
8801 GGGTCTCACC CAGACTGTTC TCTCCTCAGG ACAAAAAAGC CAGAGACATA
8851 CTTGATGCCC AAAGATGGCA AGAGTACCGC GACAGGTGAG AGGACGGGGG
8901 GCAGCCGGCG GGGGGGGACA CCCTGAGGAG ACCCAGAGTG TTCAGGGAAT
8951 GGAGCAGGGG CTGGGAGCAG GCTGGGAGGG CTCACAGCTA CCCTGCTGAA
9001 GAATTGGGTC TTTGGGCCGG GTGCGGTTGC TCATGCCTGT AATCCCAGCA
9051 GTTTGGGAGG CCGAGGCAGG TGGATCACTT GAGGTCAGGA GTTTGAGACC
9101 AGCCTGGCCA ACATGGAGAA ACCCTGTCTC TACTAAAAAT CCAAATTAGC
9151 CAGGCGTGGT GACAGGTGCC TGTAGTCCCA GCCACTTGGG AGGCTGAGGC
9201 AGGAGAATTG CTTGAACCCG GAAGACGGAG TTTGCAGTGA GCCGAGATCG
9251 TGCCACTGCA CTCCAGCCTG GGCAGCAGAG CCAGACTCCA TCTCAAAAAA
9301 AAAAAAAAAA AAGAAGAATT GGGTCTTTGG AAGGTCCCTG GAGACTGAAA
9351 GGAGCCCTTT GCAGGTGGCA GTGCAGAGAC CAGCGCAGAC CCTTGCTACT
9401 GGCAGCCGGG GGAGTGTTTG CGGCTGAATG AATGAACAGG TTTTGGAGGG
9451 CAGCGTGGCC TTCAGAGGCG ATGCAGGGCT GTGGCAGTTT CTAATACTTA
9501 TTGCACAGTC ACTGCTAATA ACAATATTAA TAATAATACC TAACATTAAT
9551 GGAGTGCTTA CTCTGTGCCA GCCACTATTT TGTTTTTGTT GTTTTCAGTG
9601 ACAGGGTCTC GCTCTGTTGC CCAGGCCAGA GTGAAGTGGT GTGATCATAG
9651 CTCACTACAG CCTCGACCTC CTGGGCTGAA GCGATCCTCC CACCTCAGCC
9701 TCCCAAGTAG CTGGGATTAC AGGTGTGTGC CACCATGTCC AGCTAATTTT
```

FIGURE 3C

```
 9751 TAATTTTCTG ATAGAGATGG GGTCTCACTA CATTGCCCAG GCTGGTCTTA
 9801 AGCTCTTGGC CTCAAGCAAC CCTCCTGCCT CAGCCTCCCA AAGTGCTGAG
 9851 ATTATAGACA TGAGCCACTG TGCCCGGCTT TTTCTTCTTC TTATAAGGAC
 9901 ACGAGGCCTG TTGGGTTAGG GCCCACTCTA CTGACCTCAT TTTAACTTAA
 9951 TTACCTCTTG AAACGTACTT AAGAGTACCT TTCTCTTAAT ACACCCACAC
10001 TGTAAGGTAC TGGGTGGTTA GGACTTCAAC ATATGAATTT TGAGAAGGCG
10051 GATGTCAGCC AATACCAAAC AGCATCAGCA CCTCCACGGT TGGATGAAGG
10101 GCTGGTCAGA AATGCACACT CAGGTCCCAC AGTGGACCTA CTGAACAGGA
10151 TAGGCATTTT AGCAAAATCC CAGGTATTCG GGTGCACCTT AAAGTTAGGA
10201 AAAGGTCAGG CACTGTGGCT CATGCCTGTA ATCCCAGCAC TTTGGGAGGC
10251 CGAGGCGGTT GAATCACCTG AGGTCAGGAG TTCGAGACCA GCCTGACCAA
10301 TATCGTGAAA CTCCATCTCT ACTAAAAATA CAAAAATTAG CCAGGTGTGG
10351 TGGCGGGTGC TTGTAGTCCC AGCTACTTGG GAGGCTGAGG CAGGTGAATT
10401 ACTTGAACCT GGGAGGTGGA GGTTGCAATG AGCCAAGATT GCACCACTGC
10451 ACTCCAGTGA CAGAGCGAGA CTCCATCTCA AAAAAAAAAA AAAAAAAGT
10501 TGGGAAAAGG CCAGGTGCAG TGGCTCCACG CCTGTAATCC CAACACTTTA
10551 AGAGGCTGAG GTGGGAGAAT CCTTTGAGCC CAGGAGTTCG AGACCAGCCT
10601 GGGCATTGTC CCAAGACCTT GTCTTTACAA AAAATTAGCC GGGTGTGGTG
10651 GCATACGTCT GTGGTCCCAG CTATTCGGGA GGCTGAGGCA GGGAGATTGC
10701 TTGAGCCTAG GAGTCTAGGG CTGTAGTGAG CTGTGATCAC GTCACTGTAC
10751 TCTAGCCTGG GCAACAGAGC AAGACTCTGT CTCCAAAAAA GAAAATAAAG
10801 TTGGGAAAGG CTCACTAACT TCATCAGATG AGAACAAAGA CATGTTTGAA
10851 GTGTGAGGCC GAAGCCTGGA GAACGCTATG CGCCCAGGAA ATGCAGGGCA
10901 GCAGAGACTC AAGATGCCAG CGCCTGTTCT GGAGGCCCAG ATGGGCCCTG
10951 CAATGCCCAC TCACCCTGCC CTCCCTCTTG CCCCAGACAT CACCGGCCCC
11001 ATCATCCTGC AGACGTACCG CGCCATTGCC GACTACGAGA AGACCTCGGG
11051 CTCCGAGATG GCTCTGTCCA CGGGGGACGT GGTGGAGGTC GTGGAGAAGA
11101 GCGAGAGCGG TCAGACCTCC CACCTTACGG GGCTCCTTCC CCTGGTGCTC
11151 AGGAACCCAC AGCCACAAGC CCCCTGCCAA GGCTCAGGCA GCCTGGCCCC
11201 TGGGAGGACT CCAGCTCTGT TAGGGGCCCT AAATGTCCTC CCCACACTGT
11251 GGGTCGCCTT CTCTCTTAGT GTGCACCCTG TGGTGGCTGT GGGCATCTGT
11301 GCATGGCAGG CCGGGGCGGG GCATGTCTGC GTGTTCTGTC TGGATGGGTA
11351 TGGGACCGTC TGTTCATTAT GAAGTGGGCT CAGAGCTGTG ATTCTGTGAG
11401 CATGTGTGCA TGCATGCATG TGACCTCATT GTCCAGTGTG GTGAAGGTGA
11451 CATTTCCAAA TCTGAGCATT GGACATCAGT GTGTCTGTGT CCCTGTGTCC
11501 TCACCATCCC TGATGGCTGC AGGGAGCCGC TGGGCCCTGC CCCTCAGTCA
11551 CATTCCCGCA CCTCTGGCAC AGGTTGGTGG TTCTGTCAGA TGAAAGCAAA
11601 GCGAGGCTGG ATCCCAGCAT CCTTCCTCGA GCCCCTGGAC AGTCCTGACG
11651 AGACGGAAGA CCCTGAGCCC AACTATGCAG GTGCCCCCTG CCCTCCGAGG
11701 CTGTAGGGGT GTGGGAGAAA GGGGCAGGCA GGGCTCAGGG ATATTGAGTG
11751 ACTGCTTTGG AGTCTGGGCT GGTTGCTGGC TTGGCAGAAA AGTCAGGGCT
11801 AAGATCTCAT CGGCTCTGGC TTGGGGGCCC TGGCAGGTTG TGATGCCCTT
11851 GGTCTGGACA GGGAACCAGG AGGAGGAGCA GACGACTCGG GAGAGTGGGA
11901 GGCCAGTGGT GTCTGTGGAT ATGTGGCCAG GTTCAGTGGG AAGCTGAAGG
11951 ATGAGCAGAC CTTAGGCTCA GGAAGGAGGG CTGCCTGGAA GTGGGGCAT
12001 CATCACTGAC CAGAAAGGGA AAACTGGCAG TGCCAGGGCT GGATGGGGCC
12051 TGCATTGAGC TTGAAAAAAA CTATAATAGA ATTGGTTACC ATTTTATTTT
12101 ATTATTTATT TATTTATTTT ACTTTTTTGA GATAGAGTCT CACTCCCTTG
12151 CTAAGGCTGG AGTGCGGTGG TGCTATCTCA GCTCACTGCA ACCTCTGCCT
12201 CCCAGGATCA AGTGATTCTC CAGCCTCAGC CTCCCCAGGT AGCTGGGATT
12251 ACAAGCATGC ACCACCATGC CTGGATAATT TTTGTATTTT TAGTTGAGAC
12301 GGGGTTTCAC CAGGTTGGCC AGACTGGTCT CGAACTTCTG ACCTCAGGTG
12351 ATCTGCCTGC CTCGGCCTCC CAAAGTGCTG GAATTACAGA TGTGAGCCAC
12401 TGTCCCTGGC CTCGTTACCC ACATTTTAAA ATGGAGTGAT TTCACCCTTT
12451 TATGTGGATT TACAGCTTGT TTTTTTTTTT TTTTGAGAC AAAGTCTGGC
12501 TCTGTCACCC AGGCTGGAGT GCAGTAATGC AATCTCAGCT CACTGCAACC
12551 TTAGCCTCCT GGGTTCAAGC AATTCTCCTG CCTCAGCCAC CTGAGTAGCC
12601 TGGGGTTACA GGCATGCACC ACCACGCCAG GCTAATTTTT TGTATTTTTA
12651 GTAGAGATGG GGTTTCGCCA TGTTGGCCAG GCTGGTCTCG AACTCCTGAC
12701 CTCAGGTGAT CCGCCCGCCT TGGCCTCCCA AAGTGCTAGG ATTACAGGTG
12751 GGAACCACCT TGCCCAGCCT GTGGCTATCG TTTAAACACT GGGAAGGCCT
12801 GCAGCCCCCA GGCCGACAGT TAGCTGCAGC TGAGCAGTTC CCAGTGCCAG
12851 GTAGACGGAT GCTCCACCCA CCTACTCATG GCTGATCTCT TGTCATAGTG
12901 AAGTGTCTGG ACAGACCTTC ATCGTTATGG GATCTCTGGT CCCCAGAGTG
12951 GGTGGCAATG AATGGGAGTG GACAAGCTCA CCTGGGTGTA GGGGGCAGAG
```

FIGURE 3D

```
13001 GGCCGAAGTC CAGAGTGTAC CCCCAGAGTG GGTGCCAGCA GGAGCTTGCC
13051 GAGGGATCTG GGATGGAGCA GGAGGGTGGA GGGAGGAGAC CCAGAAGAGG
13101 GGGAACTGTG GGCCCTGGGT GGGTCTGGAG TGCCTGGAGG AAGCCCAGGC
13151 GCAGAGAGGA GAAGATGGGA TGGGTGGCGA GCCCCAGGCT GGGCCGACCT
13201 CACACTGTGC TCTGTGCCCC TGCCGTGGAC CAGGTGAGCC ATACGTCGCC
13251 ATCAAGGCCT ACACTGCTGT GGAGGGGAC GAGGTGTCCC TGCTCGAGGG
13301 TGAAGCTGTT GAGGTAATTC CAAGGCCT GGACGGCTGG TGGGTCATCA
13351 GGTAGGAGGG CCCCTCTCCA TCCAGAGCAC CCATCTGAGT CAGCCCCAGC
13401 CAGGACGGGG TGTTTAGGGA TCTGGGTGA CTTGTCCCTG GGACTCTGGG
13451 TAAGCCACTG CCCCTCTCTG GGCTTAGTTT CCATCTCAGT AGCAGGGAGG
13501 GATGAGCCCA CCCTTGCCTG TCTTGTGGGG ATCCAATGTC CTTGTCCAAG
13551 TGGGTGCATT TCTCCTTTGT GATTTAGGGT CTCTTCCCAA CCATCTATTA
13601 TTATTCCTTC TCTGGCAACA TGGTGAACTG TTGTATAAAT AATTACATTC
13651 CTAGCTAGGC GCAATGGCCC AGGCCTGTAA TCCCAGCACT TTGGGAGCCC
13701 AGGACAGGAC GATCACGTGA GGTCAGGAGT TCGAGACCAC CCTGGCCAAC
13751 ATGGCAAAAC CCTATCTCTA CTAAAAACAC AAACATGAGC CGGGTGTTGT
13801 GGTGGGAGCC TGTAATCCCA GCTACTCGG AGTCTGAGAC AAGAGAATCA
13851 CTTCAACCCG GGAGGCGGAG GTTGCAGTGA GCCAAGATCG CGCCATTGCA
13901 CTCCAGCCTG GGCAACGAGA GCGAAACTCC GTCTCAAAAA AAAAAAAAA
13951 AAAAAAGATT ACTTTCTTTT TATCATTCCT TTATCTTTTA AAGCTTTCTT
14001 GCAGTCAGGT GCAGTGTCTC ATGCCTGTAA TCCCAACACT TTGGGAAGCT
14051 GAGGTGGGAG GATCACTCAA GGCTACAAGT TCAAGACCAA CCTGGGCAAT
14101 GTAGGGAGAC CTCTGTCTCT ACAAAAAAAA TTAAAAAATA GCTGGATGTG
14151 GTAGCACACA CCTGTAGCCC CAGCTACTCA GGAGGCTGAG GTGAAAGGAT
14201 CACTTGACCC CAGGAGTTGG AGGCAGCAGT GAGCTATGAC TGCACCACTG
14251 CACCCCAGCC TGGGTGATGG AGCAAGACCC TGTCTCAAAA AAAAAAAAA
14301 AAAAAAAGCT TCCATTGCAA TTCCCATCTG TTTATCCTCC AAATGAATGC
14351 AGAAATACTA ATTATCTTTT TTCTGGTTCT GGGGAACACA GAATTCTAGC
14401 GGCTTGTGGA GCCATTTCCC TGGAGCCATG GGGCCTCCCA GGTCCTTTCC
14451 TGTGTCTTCA TTTTTTACGA ATTTTTTCAT TTTTTGAGAC AGGATCTTGC
14501 TCTGACTCCC AGGCTGGAGC ACAATCATCG CTCACTCAAG CGATCCTCCC
14551 ACCTCAGGCT CCCACGTAGC TGGGACTACA GGTGAGCACC ACCACATCTG
14601 GCTAATGTTT TTTAATTTTT TTGTAGGGGT GGGGTCTCAC TATGGTGCCA
14651 AGACTAGTCT TAAACTCCTG GCCTCAAGAG TTCCTCCTGC CTTGGCCTCC
14701 CAAAGCACTG GGATTACAGG AATGAGCCTC CATGCTGGGC CTTTGCTGGC
14751 GTCTTCAGAG CCCTAGGTCA CAGGGCCAGC CTGGCGCCCT GCCGCAAGCT
14801 TATCTTAAAG CTGGGACCAC AACATGCATA CCTGCAGCCG GGCCCGGGGC
14851 CAGAGGGCTT TGAGGCAGCA TTTCTCAGCC TTTTAGACAC ACACTCTGTT
14901 AACCCCCATC CTGTGTCTCT GATAATCTTC TTGTGATCCT CCCACCAGCC
14951 AAGAATTGGG TTTTATGTGA ACCTTGTATT ATGCAAAGTT TTCTTTTGTT
15001 TTTTTTTTCA CTCCCAAATA TAATATTGAG AATAGAAAGA AAGTCTTTTC
15051 AACAAATGGT GCTGGAACAG ATGGATTTCC ATACTGGAAA AAAAAAAAA
15101 AGAGCAAAAA ACAAACCTAG ACCCCTTCCT CACACTGTAC ACATATGTTT
15151 ACTTCAGATG GATCACAGGT TTATCCCAGA GTAAAACCTG AAACTAAAAA
15201 CCATTTGGGG CTGGACAGGG AGCTCACGCC TGTAATCTCA GCACTTTGGG
15251 AGGCTGAGGC AGGTGGATCA CTTGATGTCA GGAGTTTGAG ACCAGCCATG
15301 ACCAATATGG TGAAATCCTG TCTCTACTAA AAAAATACAA AATTAACCAA
15351 GTGTGGTGGT GCATGCCTGT AATCCCAGCT ACTTGGGAAG CTGAGACAGG
15401 AGAATTGCTT GAACTTGGGA AGCAGAGGTT GCAATGAGTC GACATCATGC
15451 CATTGCACTC CAGCCTAGGC AACAAGAGCA AAACTCTGTC TTGGGGTTGG
15501 GTGGGGAAA AGCATTTGGA AGAAAGCATA GAATTTGGTG GCTTGGAGGT
15551 AGGCAAAGGT TCGTAGGAGA CAGAAGGCAG TTAACATAAA AGAAAAATTG
15601 GCAAATATAA TCCTGCCAGT GTCTTCTTTT TTCTTTAATT TTTTCGGGAG
15651 GTAGAGATAG GGGTCTTGCT ATGTTACCCA GGCTGATCTC CAACTCCTGG
15701 CCTCAAGCGA TCCTCCCACC TAGATCCCTC AAAGTACTGG GATTACAGGC
15751 GTGAGCGACC GTGCCCTGCC CATTCTTGCC AATGTCTTAT AGCAAATACC
15801 TGTCCCCTGC GGTGACCTGG ATCTGCTAAC CTCCACCCCT GCCTAGACTG
15851 TGGAAGGATT GCTGGAAGGG TCTCAGTTGC ACAGACCAGG AAACTGAGGC
15901 CCACAGAGGC AGGTGTCCGG TTGTTTGCAA CCTCTCAGCC TGTGCTAACC
15951 CCAATTGTTC AGAGAGAGCC CTGAAACCCT CTCCTCTGGG CGCCCCCAGG
16001 TGACTGCCCC AGCCTCAAGG GCTGCCTCTG TTGCAGGAAA GACGACGTCA
16051 CAGGCTACTT CCCGTCCATG TACCTGCAAA AGTCAGGGCA AGACGTGTCC
16101 CAGGCCCAAC GCCAGATCAA GCGGGGGGCG CCGCCCCGCA GGTAAGCGGG
16151 GGTCCCCGGG GCTGGGCGGG GTCGAGCGGG GCGCACCACG GGTTCGCTCT
16201 GTCTAGGCCA TAGCTTGGCA GTGCCGGGGC GGGGGCTCTC AGCCTGGCAG
```

FIGURE 3E

```
16251 GAGAGGCAGG ACCCTCACGG GGGAAAGGGG CTGGACGCGC CTGGCCGCGG
16301 TGTGGGGCTG GCACGGGGGC GGAAGGAAAG CGGCGATGCC CGGGGGCTTT
16351 GGGGATGGGC AGTCCAGGGG GGCTCCCCGG AGAGGGGGAC GACAGACCGA
16401 AGGCTGGTGA GGGGCGTGGA AAACCGCCCA GGCTCTGCTG CAGGGCAAGG
16451 GTCCTTGTCG TGACGGGGGC AGCCGCCTCT TGTCCCGCCG GGGTCGTGCA
16501 GACTACCGGC CCCCTACTGC CCCCCACTTC CTCGGACCAG GGGTGCCCAT
16551 CTGAGTCCCT GGGGGCAGGG GCGCCCTCGG GCTTTGACGA CGCCCCGTCC
16601 CGCTGGGCCA GGTCGTCCAT CCGCAACGCG CACAGCATCC ACCAGCGGTC
16651 GCGGAAGCGC CTCAGCCAGG ACGCCTATCG CCGCAACAGC GTCCGTTTTC
16701 TGCAGCAGCG ACGCCGCCAG GCGCGGCCGG GACCGCAGAG CCCCGGGAGC
16751 CCGCTCGGTG AGTGCAGCGG GAGAGGGCAG GAAGGGCAAG CCCTAGGGGC
16801 GGAGTCAGCG GGAGAGGCGG GGCCAGAGGC AGGGCCAGAG TAGCGGGGCG
16851 GGACCAGAGG GCGGAATCAG AGGGAGAGGC GGGGACTGGA GGCGGGGGCA
16901 GAGGAGGAGC CAGCGCTAGG GGGCGGAGCG ATCCCTAAGA GGCGGAGTCA
16951 GAGGGAGAGG CACAAGCGGG AGGCGAGGCC AGAGCGCGGA GCAGGAGTTG
17001 GAGACCGCGC CGGGGCGAGG CCAGAGAGCG CTGTGGGCGG GGCCAGTGTG
17051 CGGGGCGGGG CGTCTGACTC GGCCCCGCTC TCTGCCCGCA GAGGAGGAGC
17101 GGCAGACGCA GCGCTCTAAA CCGCAGCCGG CGGTGCCCCC GCGGCCGAGC
17151 GCCGACCTCA TCCTGAACCG CTGCAGCGAG AGCACCAAGC GGAAGCTGGC
17201 GTCTGCCGTC TGAGGCTGGA GCGCAGTCCC CAGCTAGCGT CTCGGCCCTT
17251 GCCGCCCCGT GCCTGTATAT ACGTGTTCTA TAGAGCCTGG CGTCTGGACG
17301 CCGAGGGCAG CCCCGACCCC TGTCCAGCGC GGCTCCCGCC ACCCTCAATA
17351 AATGTTGCTT GGAGTGGACC GAGGCTCTGC AGGAATGCAG GGAGGGCCGG
17401 GCTCCGCCCC AGGGTTATTT TCTAAGTTGA GGACAGGGAG GTTGTGAGTT
17451 CTGNNNNNNN NNNNNNNNNN NNNNNNNNNN NNNNNNNNNN NNNNNNNNNN
17501 NNNNNNNNNN NNNNNNNNNN NNNNNNNNNN NNNNNNNNNN NNNNNNNNNN
17551 NNNNNNNNNN NNNNNNNNNN NNNNNNNNNN NNNNNNNNNN NNNNNNNNNN
17601 NNNNNNNNNN NNNNNNNNNN NNNNNNNNNN NNNNNNNNNN NNNNNNNNNN
17651 NNNNNNNNNN NNNNNNNNNN NNNNNNNNNN NNNNNNNNNN NNNNNNNNNN
17701 NNNNNNNNNN NNNNNNNNNN NNNNNNNNNN NNNNNNNNNN NNNNNNNNNN
17751 NNNNNNNNNN NNNNNNNNNN NNNNNNNNNN NNNNNNNNNN NNNNNNNNNN
17801 NNNNNNNNNN NNNNNNNNNN NNNNNNNNNN NNNNNNNNNN NNNNNNNNNN
17851 NNNNNNNNNN NNNNNNNNNN NNNNNNNNNN NNNNNNNNNN NNNNNNNNNN
17901 NNNNNNNNNN NNNNNNNNNN NNNNNNNNNN NNNNNNNNNN NNNNNNNNNN
17951 NNNNNNNNNN NNNNNNNNNN NNNNNNNNNN NNNNNNNNNN NNNNNNNNNN
18001 NNNNNNNNNN NNNNNNNNNN NNNNNNNNNN NNNNNNNNNN NNNNNNNNNN
18051 NNNNNNNNNN NNNNNNTAAA AATTAGCTGG GCGTGGTGGC ATGCATCCAC
18101 AATCCCAGCT ACTGGGGAGG CTGAGGCATG AGAATCGCTT GAACCGGGGA
18151 GGCAGATGTT GCAGTGAGCC GAGACGGCGC CACTGCACTC CAGCCTGGAC
18201 TACAGAGCGA GACTCTATCT CAAAAAAAAA AAAAAAAAAA AAGTAACTTA
18251 GGTGCAGGGT GTCCTCTGTT ATTCACTGAG ACCGTGCCCC GGTTATGAGG
18301 TTGTACCAGA AAGCAAGTAT TCACTATGCA CACTATTCAC CGCTCACCCT
18351 AGCATTGAAG CCAGCCTGTA GCCTGAAAGC CTTTGCTTTG AGGGCAGGTC
18401 TTTCCCCAAA ATGCAGACAC GAAGGTGCAA AGTGAAGCTG CCAGTCTTGC
18451 AAAAGATGTA ACTTGTCACG AAGGCCACGA GTGGCAGGGA GAGCTGTCCC
18501 ACATTTGCGG AAGTGGCTAT GTGAGGACGG GGGAGGCGGG TCCCTTAGAG
18551 ATAAGAGACA ATCATAAGGG GAGATATCAG AGAAAATCGT AAGGGGAGCA
18601 GATGGTTGTC AAGAGAATAG GCTGACCATC GAAGGACTGG CAGAAGCTTT
18651 CAGAAAACCA CTGGACGGCT GGGCACAGTG GCTTAGGCCT GTAATCCCAG
18701 CACTTTGGGA GGCTGACGCA GGTGAATCAC TTGAGGTCAG GAGTTCCAGA
18751 CCAGCCTGGC CAACATGGTG AAACCCCATC TCTACAGAAA ATATAAAAAT
18801 TAGCCAGGCG TGGTGGCACA AGCCTAGAAT CCCAGCTACT TGGGAGGCTG
18851 AGG
(SEQ ID NO: 3)

FEATURES:
Start:    2038
Exon:     2038-2109
Intron:   2110-4800
Exon:     4801-4805
Intron:   4806-5298
Exon:     5299-5377
Intron:   5378-7131
Exon:     7132-7207
Intron:   7208-7306
```

FIGURE 3F

Exon:     7307-7472
Intron:   7473-8829
Exon:     8830-8885
Intron:   8886-10986
Exon:     10987-11109
Intron:   11110-11572
Exon:     11573-11680
Intron:   11681-13233
Exon:     13234-13339
Intron:   13340-16036
Exon:     16037-16141
Intron:   16142-16611
Exon:     16612-16757
Intron:   16758-17091
Exon:     17092-17210
Stop:     17211

SNPs:

| DNA Position | Major | Minor | Domain | Protein Position | Major | Minor |
|---|---|---|---|---|---|---|
| 139 | T | C | Beyond ORF(5') | | | |
| 262 | T | C | Beyond ORF(5') | | | |
| 43 | A | G | Beyond ORF(5') | | | |
| 344 | G | A | Beyond ORF(5') | | | |
| 721 | A | G | Beyond ORF(5') | | | |
| 1038 | A | - | Beyond ORF(5') | | | |
| 1468 | A | G T | Beyond ORF(5') | | | |
| 2758 | G | T | Intron | | | |
| 2890 | G | A | Intron | | | |
| 3304 | G | A T | Intron | | | |
| 3896 | C | T | Intron | | | |
| 3906 | - | C G | Intron | | | |
| 3907 | - | T | Intron | | | |
| 3911 | - | T | Intron | | | |
| 3932 | - | A | Intron | | | |
| 3934 | - | T | Intron | | | |
| 3949 | C | T | Intron | | | |
| 3994 | A | G | Intron | | | |
| 6272 | C | T | Intron | | | |
| 6427 | T | C | Intron | | | |
| 6694 | T | C | Intron | | | |
| 7741 | C | T | Intron | | | |
| 8294 | A | G | Intron | | | |
| 9313 | A | - G | Intron | | | |
| 10838 | G | A | Intron | | | |
| 11093 | G | A | Exon | 187 | E | E |
| 11195 | T | G | Intron | | | |
| 11213 | G | A | Intron | | | |
| 11263 | C | G | Intron | | | |
| 13707 | G | A | Intron | | | |
| 14629 | G | A | Intron | | | |
| 14698 | T | A | Intron | | | |
| 16095 | C | T G | Exon | 284 | P | S A |
| 16266 | C | T | Intron | | | |
| 16629 | C | T | Exon | 305 | P | L |
| 16642 | C | T | Exon | 309 | H | H |
| 18537 | C | T | Beyond ORF(3') | | | |
| 18589 | G | A | Beyond ORF(3') | | | |
| 18720 | G | A | Beyond ORF(3') | | | |
| 18782 | C | T | Beyond ORF(3') | | | |
| 18841 | C | T | Beyond ORF(3') | | | |

FIGURE 3G

Context:

DNA
Position

139
TACTAAAAATACAAAATTAGCCAGGCGTGGTGGCGCACACCTGTAATCCCAGCTACTTGG
GAAGCTGAGGCAGGAGAATCGCTTGAACCTGGAAGGCAGAGGTTGCAGTGAGCCGAGATT
GTGCCACTGCACTCCAGC
[T,C]
TGGGCAACAAGAGCGAAACTTCGCTTCAAACAAATAAATTAACGCCCAGCATGTCTTGGC
TTTCATCTGCCAGACCTCAACCCTCACCCCCAGGAGATCAGGTCCGGACCATGAGCTGAC
CCTGGACTCAGGCAAGGGTGAGTTGGTGCAGCCCTGGCCTGCTGGGAGGCACAGGCTGCA
GCAGGCTGCCTGGGGCTGAGGCCCGCCACTCATGAACTCATGACCTTGAATGAGCTCCAA
AAGCTCTGGGCCTCCCAGGCTCTAGGGGGAGTGGGAGAGAGAGGCCTCAGCCTGTCCCTG

262
TACTAAAAATACAAAATTAGCCAGGCGTGGTGGCGCACACCTGTAATCCCAGCTACTTGG
GAAGCTGAGGCAGGAGAATCGCTTGAACCTGGAAGGCAGAGGTTGCAGTGAGCCGAGATT
GTGCCACTGCACTCCAGCCTGGGCAACAAGAGCGAAACTTCGCTTCAAACAAATAAATTA
ACGCCCAGCATGTCTTGGCTTTCATCTGCCAGACCTCAACCCTCACCCCCAGGAGATCAG
GTCCGGACCATGAGCTGACCC
[T,C]
GGACTCAGGCAAGGGTGAGTTGGTGCAGCCCTGGCCTGCTGGGAGGCACAGGCTGCAGCA
GGCTGCCTGGGGCTGAGGCCCGCCACTCATGAACTCATGACCTTGAATGAGCTCCAAAAG
CTCTGGGCCTCCCAGGCTCTAGGGGGAGTGGGAGAGAGAGGCCTCAGCCTGTCCCTGGGC
ATGCTGCCCCCTCCTCACCTCTTTGTCCCAAATCCCCTTCCTGGCAAAGCTGACAGTCTT
AATATCACTCTGGAGAAAACTGAGTCAGCCCTAAGGAACAATTCAATGA

43
TACTAAAAATACAAAATTAGCCAGGCGTGGTGGCGCACACCT
[A,G]
TAATCCCAGCTACTTGGGAAGCTGAGGCAGGAGAATCGCTTGAACCTGGAAGGCAGAGGT
TGCAGTGAGCCGAGATTGTGCCACTGCACTCCAGCCTGGGCAACAAGAGCGAAACTTCGC
TTCAAACAAATAAATTAACGCCCAGCATGTCTTGGCTTTCATCTGCCAGACCTCAACCCT
CACCCCCAGGAGATCAGGTCCGGACCATGAGCTGACCCTGGACTCAGGCAAGGGTGAGTT
GGTGCAGCCCTGGCCTGCTGGGAGGCACAGGCTGCAGCAGGCTGCCTGGGGCTGAGGCCC

344
TAATCCCAGCTACTTGGGAAGCTGAGGCAGGAGAATCGCTTGAACCTGGAAGGCAGAGGT
TGCAGTGAGCCGAGATTGTGCCACTGCACTCCAGCCTGGGCAACAAGAGCGAAACTTCGC
TTCAAACAAATAAATTAACGCCCAGCATGTCTTGGCTTTCATCTGCCAGACCTCAACCCT
CACCCCCAGGAGATCAGGTCCGGACCATGAGCTGACCCTGGACTCAGGCAAGGGTGAGTT
GGTGCAGCCCTGGCCTGCTGGGAGGCACAGGCTGCAGCAGGCTGCCTGGGGCTGAGGCCC
[G,A]
CCACTCATGAACTCATGACCTTGAATGAGCTCCAAAAGCTCTGGGCCTCCCAGGCTCTAG
GGGGAGTGGGAGAGAGAGGCCTCAGCCTGTCCCTGGGCATGCTGCCCCCTCCTCACCTCT
TTGTCCCAAATCCCCTTCCTGGCAAAGCTGACAGTCTTAATATCACTCTGGAGAAAACTG
AGTCAGCCCTAAGGAACAATTCAATGAACCATTTGCTTACTTGAGGATTGGAACTCAAGT
CTCACTCAAAGTCTGTGCCATTTTCGTCCCAGCTGTCACTGGCCCTCATCCACACACACC

721
AGGCCTCAGCCTGTCCCTGGGCATGCTGCCCCCTCCTCACCTCTTTGTCCCAAATCCCCT
TCCTGGCAAAGCTGACAGTCTTAATATCACTCTGGAGAAAACTGAGTCAGCCCTAAGGAA
CAATTCAATGAACCATTTGCTTACTTGAGGATTGGAACTCAAGTCTCACTCAAAGTCTGT
GCCATTTTCGTCCCAGCTGTCACTGGCCCTCATCCACACACACCCAAGGATGAGCATCTA
ACGCTTGCATGCACACTCCCATGCCCGCGTTCATTCACTCATTCATTCATTCATTCACTC
[A,G]
TTCATTGACTCATTCATTCATTCACTCACTCATTCATTCACTCAGTGAATGTTGCAGTCA
CGATCCAAATATTTATGGCCTCTGTGTGCCAGGCACTAGATGGAGGGGCTGGGGCTAGAG
CCCCTGATAACCCGGTCATGCCCTAGCTTTCCTGGGACACACATTGTGGTAAGGGGAGAC
TAAAAAAATTAAGTCAGGCCAGGCACGGTGGCTCATGCCTGAATCCCAGCACTTTGGGAG
GCCGAGGCGAGTGAATTACCTGAGGTCAGGAGTTCAAGACCAGCCTGGCCAACATGGAGA

1038
TTCATTCACTCACTCATTCATTCACTCAGTGAATGTTGCAGTCACGATCCAAATATTTAT
GGCCTCTGTGTGCCAGGCACTAGATGGAGGGGCTGGGGCTAGAGCCCCTGATAACCCGGT
CATGCCCTAGCTTTCCTGGGACACACATTGTGGTAAGGGGAGACTAAAAAAATTAAGTCA
GGCCAGGCACGGTGGCTCATGCCTGAATCCCAGCACTTTGGGAGGCCGAGGCGAGTGAAT
TACCTGAGGTCAGGAGTTCAAGACCAGCCTGGCCAACATGGAGAAACCCAGTCTCTAATT
[A,-]

FIGURE 3H

```
        AAAAAAAAAAAAAAAATTAGCCAGGTGTGGTGGCACATGCCTGTAATCCCAGCTACTCAGG
        AGACTAACGCAAGAGAATTGCTTGAACCCAGGAGGCAGAGGTTGCGGTGAGCCGAGATCG
        CGCCATTGCACTCCAGCCTGGGAAACAAGAGCGAGACTCCATCTCAAAAAAAAAAAAAGT
        GGGGAGGCAGAGGCAGGAGGATCACTAGAGGCCAGTAGTTTGAGACCATCCTGGGCAACAT
        AGCAGGACCCTGTCTGTACAAAAAAATTAAAAAAAATTTAACCGGGCATGGTGGCACACA

1468    ACTCCAGCCTGGGAAACAAGAGCGAGACTCCATCTCAAAAAAAAAAAAAGTGGGAGGCAG
        AGGCAGGAGGATCACTAGAGGCCAGTAGTTTGAGACCATCCTGGGCAACATAGCAGGACC
        CTGTCTGTACAAAAAAATTAAAAAAAATTTAACCGGGCATGGTGGCACACACCCGTAGTC
        CCAGCTACTCCAGAGGCTGAGGCAGGAGGATCGCTGGAGCCCAGGAGTTGGAGGCTGCAG
        TGAACTGTGATCCCACCACTGCACTTAAGCCTGGATAACAAAGCAAGACCCTGTCTCAAA
        [A,G,T]
        AACAATAGCAATAATAATAAAGAAAAATTAAATGCAATTTGCGATGCATCAGTGATAAGT
        GCTCTGCAGAAAAAGGAGGCAGGAAGAGGCTGAGAAAGGTATGAGGTTTGCTATGCAATG
        TGAAGTTATCAAGGAAGGCTTCTCGGAAGAGGTGACATTTGAGCAGAGAAATGGAGGAGA
        GTTATGGAGGGAAGATGGTGAATGGGGGGAACATGGTCAAGACCAGGAATATGGTCAAGG
        GGGGAAAGATGGTCAAGGGGACGCAGCAAATGCAAAGGCCCTGAGGCAGGAGCAGCTTGA

2758    TCAGAGAGTGGCCCTCCCAAGAGGGAGGCCTGGAAACTAAAGCTCTCTCTCTCCCCAGCT
        GCCTGTAGTGTCAGTTAGAGTCTTATCCTCTCCAGTAGGGTGACACCATGACAGGGGCCA
        ATAGAGTCCTCCCATCTGTCCCCAAGGAGGCTGGACAAATGCCTGCTCAGACACACAAGT
        CCACTGGGTCCCCTAATCCCATAGGAAGGCCAGGGAGGAACTACATTTAGGAAATTGAAG
        CTTGTATGGAACATTTAGTCCTATGTGCCAAGACCTTTCTCTTTTTTGTTATTTTTTGT
        [G,T]
        TTTTGAGACAGAGTCTTGATCTGTTGCCCAGGCCAGAGTGCAGTGGCACGATCTCAGCTC
        ACTGCAACCTCCGCCTTCCAGGTTCAACTGGTTCTCCTGCCTCAGCCTCCAGAGTAGTTG
        GGATTACAGGTGCCCACCACCACGCCTGGCTAATTTTTTGTATTTTTAGTAGAGACAGGGT
        TTCACCATGTTGGCCAGACTGGTCTCAAACTCCTGACCTCAAGTGATCCACCCACCTGGG
        CCTCCCAAAGTGCTGGGATTACAGGCATGAGCCACCGTGCCTGGCCTGTTTTTTTGAAAT

2890    CATCTGTCCCCAAGGAGGCTGGACAAATGCCTGCTCAGACACACAAGTCCACTGGGTCCC
        CTAATCCCATAGGAAGGCCAGGGAGGAACTACATTTAGGAAATTGAAGCTTGTATGGAAC
        ATTTAGTCCTATGTGCCAAGACCTTTCTCTTTTTTGTTATTTTTTGTGTTTTGAGACAG
        AGTCTTGATCTGTTGCCCAGGCCAGAGTGCAGTGGCACGATCTCAGCTCACTGCAACCTC
        CGCCTTCCAGGTTCAACTGGTTCTCCTGCCTCAGCCTCCAGAGTAGTTGGGATTACAGGT
        [G,A]
        CCCACCACCACGCCTGGCTAATTTTTTGTATTTTTAGTAGAGACAGGGTTTCACCATGTTG
        GCCAGACTGGTCTCAAACTCCTGACCTCAAGTGATCCACCCACCTGGGCCTCCCAAAGTG
        CTGGGATTACAGGCATGAGCCACCGTGCCTGGCCTGTTTTTTTGAAATGAGGTCTGGAGT
        GCAGTGGTGCGATCATAGTTCACTGCAGCCTCAACCTCCCAGGCCCAAGTGATCCTCCTG
        CCTCAGCCCCTTGAGTAGCTGGGGCTACAGGCGCACACCACCATGCCTGGCTAGTTTTTA

3304    CAAAGTGCTGGGATTACAGGCATGAGCCACCGTGCCTGGCCTGTTTTTTTGAAATGAGGT
        CTGGAGTGCAGTGGTGCGATCATAGTTCACTGCAGCCTCAACCTCCCAGGCCCAAGTGAT
        CCTCCTGCCTCAGCCCCTTGAGTAGCTGGGGCTACAGGCGCACACCACCATGCCTGGCTA
        GTTTTTAAAATTTTTGTGGAGATGAGGTTTCACTATGTTGTCCAGGCTAATCTTGAACTC
        CTCGGCTTAAGCAACCCTCTGGTCTCAGCCTCCCACAGTGCTAGGATTACAAGCGTGAGC
        [G,A,T]
        ACCGTGCCTAGTCACTTTTCTCCTTTTCTTTGTAACTTTCAGTTTTGAAATTTCAAATTT
        ACAGAAAGGCTACTGGGTGTCAAAACGGTACCAGTCACTCCAATAGTCTTTCACTCACCT
        TCATCCACACCTCTCTTTCTGGGGATATTTTCTGAATTATTTGAGAGTGAGTTGAAGACG
        TGTTTCTTTACCTCTAAATACTAGTTGTTGGGCATTTCTTAAAATCAAGGCATTCTCTTA
        CATAATCACAACACACGTGTCAAAATCAGGAAATTAACATGGACAAAACACCATTATCCA

3896    CATTATCCACCCACAGACTTTACTGAGGTTTCCCCGATTATCCTGCTTGTCCTCTGCAGT
        GAAAACTTTTTTCAGGTCTAGGATCCAGTCAAGGATCAATGTCATAGCCTTTAACCTTCT
        TTAATCTGGATCAGTCTTTTTTCTTTTTCTTTTTCTTTTTTGGACACGGAATCTCACTC
        TGTCGCCAGACTGGAGTGCAGTGGTGCAATCTCGGCTCATTGCAACCTCTGCCTCCTGGG
        TTCAAGAGATTCTCCTGCCTCAGCCTCCTGAGTAGCTGGGAATACAGGTGCGCGCCACCA
        [C,T]
        GCCCAGCTCGTTTTTGGTAGAGACAGGGTTTTGCCATTGATTCTGGATCAGTCTTTTTTT
        TTTTTTTTATGAGATGGAGTCTTACTCTGTCACCCAGGCTGGAGTGCAATGGCACAATCT
        CCACTGCACTGCCATCCTCCGCCTCCCAGGTTCAAGCAATTCTCGTGCCTCAGCCTCCCGAG
        TAGCTGGGATTACAGGCATGCGCCACCATGCCCGGCTACTTTTTGTATTTTTAGTAGAGA
        CAGGGTTTCACCATGTTAGCCAGGCTGATCTCGAACTCCTGACGTCAGGTGATCTGCCCG
```

FIGURE 3I

| | |
|---|---|
| 3906 | CCACAGACTTTACTGAGGTTTCCCCGATTATCCTGCTTGTCCTCTGCAGTGAAAACTTTT<br>TTCAGGTCTAGGATCCAGTCAAGGATCAATGTCATAGCCTTTAACCTTCTTTAATCTGGA<br>TCAGTCTTTTTTCTTTTTCTTTTTCTTTTTTTGGACACGGAATCTCACTCTGTCGCCAGA<br>CTGGAGTGCAGTGGTGCAATCTCGGCTCATTGCAACCTCTGCCTCCTGGGTTCAAGAGAT<br>TCTCCTGCCTCAGCCTCCTGAGTAGCTGGGAATACAGGTGCGCGCCACCACGCCCAGCTC<br>[-,C,G]<br>TTTTTGGTAGAGACAGGGTTTTGCCATTGATTCTGGATCAGTCTTTTTTTTTTTTTTTAT<br>GAGATGGAGTCTTACTCTGTCACCCAGGCTGGAGTGCAATGGCACAATCTCCACTCACTG<br>CATCCTCCGCCTCCCAGGTTCAAGCAATTCTCGTGCCTCAGCCTCCCGAGTAGCTGGGAT<br>TACAGGCATGCGCCACCATGCCCGGCTACTTTTTGTATTTTTAGTAGAGACAGGGTTTCA<br>CCATGTTAGCCAGGCTGATCTCGAACTCCTGACGTCAGGTGATCTGCCCGCCTCGACCTC |
| 3907 | CACAGACTTTACTGAGGTTTCCCCGATTATCCTGCTTGTCCTCTGCAGTGAAAACTTTTT<br>TCAGGTCTAGGATCCAGTCAAGGATCAATGTCATAGCCTTTAACCTTCTTTAATCTGGAT<br>CAGTCTTTTTTCTTTTTCTTTTTCTTTTTTGGACACGGAATCTCACTCTGTCGCCAGAC<br>TGGAGTGCAGTGGTGCAATCTCGGCTCATTGCAACCTCTGCCTCCTGGGTTCAAGAGATT<br>CTCCTGCCTCAGCCTCCTGAGTAGCTGGGAATACAGGTGCGCGCCACCACGCCCAGCTCG<br>[-,T]<br>TTTTGGTAGAGACAGGGTTTTGCCATTGATTCTGGATCAGTCTTTTTTTTTTTTTTATG<br>AGATGGAGTCTTACTCTGTCACCCAGGCTGGAGTGCAATGGCACAATCTCCACTCACTGC<br>ATCCTCCGCCTCCCAGGTTCAAGCAATTCTCGTGCCTCAGCCTCCCGAGTAGCTGGGATT<br>ACAGGCATGCGCCACCATGCCCGGCTACTTTTTGTATTTTTAGTAGAGACAGGGTTTCAC<br>CATGTTAGCCAGGCTGATCTCGAACTCCTGACGTCAGGTGATCTGCCCGCCTCGACCTCC |
| 3911 | GACTTTACTGAGGTTTCCCCGATTATCCTGCTTGTCCTCTGCAGTGAAAACTTTTTTCAG<br>GTCTAGGATCCAGTCAAGGATCAATGTCATAGCCTTTAACCTTCTTTAATCTGGATCAGT<br>CTTTTTTCTTTTTCTTTTTCTTTTTTTGGACACGGAATCTCACTCTGTCGCCAGACTGGA<br>GTGCAGTGGTGCAATCTCGGCTCATTGCAACCTCTGCCTCCTGGGTTCAAGAGATTCTCC<br>TGCCTCAGCCTCCTGAGTAGCTGGGAATACAGGTGCGCGCCACCACGCCCAGCTCGTTTT<br>[-,T]<br>GGTAGAGACAGGGTTTTGCCATTGATTCTGGATCAGTCTTTTTTTTTTTTTTTTATGAGAT<br>GGAGTCTTACTCTGTCACCCAGGCTGGAGTGCAATGGCACAATCTCCACTCACTGCATCC<br>TCCGCCTCCCAGGTTCAAGCAATTCTCGTGCCTCAGCCTCCCGAGTAGCTGGGATTACAG<br>GCATGCGCCACCATGCCCGGCTACTTTTTGTATTTTTAGTAGAGACAGGGTTTCACCATG<br>TTAGCCAGGCTGATCTCGAACTCCTGACGTCAGGTGATCTGCCCGCCTCGACCTCCCAAA |
| 3932 | ATTATCCTGCTTGTCCTCTGCAGTGAAAACTTTTTTCAGGTCTAGGATCCAGTCAAGGAT<br>CAATGTCATAGCCTTTAACCTTCTTTAATCTGGATCAGTCTTTTTTCTTTTTCTTTTTCT<br>TTTTTTGGACACGGAATCTCACTCTGTCGCCAGACTGGAGTGCAGTGGTGCAATCTCGGC<br>TCATTGCAACCTCTGCCTCCTGGGTTCAAGAGATTCTCCTGCCTCAGCCTCCTGAGTAGC<br>TGGGAATACAGGTGCGCGCCACCACGCCCAGCTCGTTTTTTGGTAGAGACAGGGTTTTGCC<br>[-,A]<br>TTGATTCTGGATCAGTCTTTTTTTTTTTTTTTATGAGATGGAGTCTTACTCTGTCACCCA<br>GGCTGGAGTGCAATGGCACAATCTCCACTCACTGCATCCTCCGCCTCCCAGGTTCAAGCA<br>ATTCTCGTGCCTCAGCCTCCCGAGTAGCTGGGATTACAGGCATGCGCCACCATGCCCGGC<br>TACTTTTTGTATTTTTAGTAGAGACAGGGTTTCACCATGTTAGCCAGGCTGATCTCGAAC<br>TCCTGACGTCAGGTGATCTGCCCGCCTCGACCTCCCAAAGTGCTGGGATTACAGGCGTGA |
| 3934 | TATCCTGCTTGTCCTCTGCAGTGAAAACTTTTTTCAGGTCTAGGATCCAGTCAAGGATCA<br>ATGTCATAGCCTTTAACCTTCTTTAATCTGGATCAGTCTTTTTTCTTTTTCTTTTTCTTT<br>TTTTGGACACGGAATCTCACTCTGTCGCCAGACTGGAGTGCAGTGGTGCAATCTCGGCTC<br>ATTGCAACCTCTGCCTCCTGGGTTCAAGAGATTCTCCTGCCTCAGCCTCCTGAGTAGCTG<br>GGAATACAGGTGCGCGCCACCACGCCCAGCTCGTTTTTGGTAGAGACAGGGTTTTGCCAT<br>[-,T]<br>GATTCTGGATCAGTCTTTTTTTTTTTTTTATGAGATGGAGTCTTACTCTGTCACCCAGG<br>CTGGAGTGCAATGGCACAATCTCCACTCACTGCATCCTCCGCCTCCCAGGTTCAAGCAAT<br>TCTCGTGCCTCAGCCTCCCGAGTAGCTGGGATTACAGGCATGCGCCACCATGCCCGGCTA<br>CTTTTTGTATTTTTAGTAGAGACAGGGTTTCACCATGTTAGCCAGGCTGATCTCGAACTC<br>CTGACGTCAGGTGATCTGCCCGCCTCGACCTCCCAAAGTGCTGGGATTACAGGCGTGAGC |
| 3949 | CTGCAGTGAAAACTTTTTTCAGGTCTAGGATCCAGTCAAGGATCAATGTCATAGCCTTTA<br>ACCTTCTTTAATCTGGATCAGTCTTTTTTCTTTTTCTTTTTCTTTTTTTGGACACGGAAT<br>CTCACTCTGTCGCCAGACTGGAGTGCAGTGGTGCAATCTCGGCTCATTGCAACCTCTGCC<br>TCCTGGGTTCAAGAGATTCTCCTGCCTCAGCCTCCTGAGTAGCTGGGAATACAGGTGCGC |

FIGURE 3J

```
             GCCACCACGCCCAGCTCGTTTTTGGTAGAGACAGGGTTTTGCCATTGATTCTGGATCAGT
             [C,T]
             TTTTTTTTTTTTTTTTATGAGATGGAGTCTTACTCTGTCACCCAGGCTGGAGTGCAATGGC
             ACAATCTCCACTCACTGCATCCTCCGCCTCCCAGGTTCAAGCAATTCTCGTGCCTCAGCC
             TCCCGAGTAGCTGGGATTACAGGCATGCGCCACCATGCCCGGCTACTTTTTGTATTTTTA
             GTAGAGACAGGGTTTCACCATGTTAGCCAGGCTGATCTCGAACTCCTGACGTCAGGTGAT
             CTGCCCGCCTCGACCTCCCAAAGTGCTGGGATTACAGGCGTGAGCCACCGTGCCAGCGGA

3994    ATGTCATAGCCTTTAACCTTCTTTAATCTGGATCAGTCTTTTTTCTTTTTCTTTTTCTTT
             TTTTGGACACGGAATCTCACTCTGTCGCCAGACTGGAGTGCAGTGGTGCAATCTCGGCTC
             ATTGCAACCTCTGCCTCCTGGGTTCAAGAGATTCTCCTGCCTCAGCCTCCTGAGTAGCTG
             GGAATACAGGTGCGCGCCACCACGCCCAGCTCGTTTTTGGTAGAGACAGGGTTTTGCCAT
             TGATTCTGGATCAGTCTTTTTTTTTTTTTTTATGAGATGGAGTCTTACTCTGTCACCCAG
             [A,G]
             CTGGAGTGCAATGGCACAATCTCCACTCACTGCATCCTCCGCCTCCCAGGTTCAAGCAAT
             TCTCGTGCCTCAGCCTCCCGAGTAGCTGGGATTACAGGCATGCGCCACCATGCCCGGCTA
             CTTTTTGTATTTTTAGTAGAGACAGGGTTTCACCATGTTAGCCAGGCTGATCTCGAACTC
             CTGACGTCAGGTGATCTGCCCGCCTCGACCTCCCAAAGTGCTGGGATTACAGGCGTGAGC
             CACCGTGCCAGCGGATTCTGGATCGGTCTTAATCAGTCTTTGTCTTTTGCAACTTTGATG

6272    AAAGTAAAACAGACAGGATCTCCCAGAACCTTCCTAGAATGGAACCATTCTTGTCGCTTT
             TGAAAAACAAAGCCAAGTTCTAGATCCCAAATAAATGCACCTGCTGGTGAACATTCTCCT
             TGTGGTTCTCGTCCCTATGTTAGTTATTTTCCTAAATTTTACATTTGTACCTTTTTAAGA
             ATGAGTTATCAGTTTTTTTATATTTGCTTTTCTTTTGAGATGGGGTCTTGCTCTGTCACC
             CAGGCTGGGGTGCAGTGGTGCAATCACGGCTCACTGCAGCCTCAACCTCCAGGGCTGAAG
             [C,T]
             GATTCTCCCATCTCAGCCTCCCATGTTGAGATCACAGGTGTGCACCACCACACCTGGCTC
             CTTTTCCTGATTTGTTTTTTGTAGAGATGGGATTTCGCTATGTTGCCCAGGCTGGTCTCT
             AACTCCTGGACTCAAGTGATCCTCCCGCCTCAGCTTCCCAAATTGCTAGGATTACAGGTT
             TGAGCCCCTGCACCTGGTCAACCTGAGTTTTAAGAGGATCCCTTTGGCGACTGGATTGAG
             GACAGACAAGAGTGGACGGGGGACACAAGGAGGCCATTTTCGTTATCCAGGCCTGGTAGT

6427    ATTTTACATTTGTACCTTTTTAAGAATGAGTTATCAGTTTTTTTATATTTGCTTTTCTTT
             TGAGATGGGGTCTTGCTCTGTCACCCAGGCTGGGGTGCAGTGGTGCAATCACGGCTCACT
             GCAGCCTCAACCTCCAGGGCTGAAGCGATTCTCCCATCTCAGCCTCCCATGTTGAGATCA
             CAGGTGTGCACCACCACACCTGGCTCCTTTTCCTGATTTGTTTTTTGTAGAGATGGGATT
             TCGCTATGTTGCCCAGGCTGGTCTCTAACTCCTGGACTCAAGTGATCCTCCCGCCTCAGC
             [T,C]
             TCCCAAATTGCTAGGATTACAGGTTTGAGCCCCTGCACCTGGTCAACCTGAGTTTTAAGA
             GGATCCCTTTGGCGACTGGATTGAGGACAGACAAGAGTGGACGGGGGACACAAGGAGGCC
             ATTTTCGTTATCCAGGCCTGGTAGTGGCTAGGGCCAGGAGGGTGGGGTTGGTGGGAAGCA
             GTCAGATCCCAAAGAGATTTGGGGATTGGAAGCAAAAGGATTTGCTGGTGACTTGCACAT
             GGGAGGGAGAGAGGTCAGTGCCTCTGTTAATCAAGGAATCCAGATTGCCACCGAAATTTC

6694    ACTCCTGGACTCAAGTGATCCTCCCGCCTCAGCTTCCCAAATTGCTAGGATTACAGGTTT
             GAGCCCCTGCACCTGGTCAACCTGAGTTTTAAGAGGATCCCTTTGGCGACTGGATTGAGG
             ACAGACAAGAGTGGACGGGGGACACAAGGAGGCCATTTTCGTTATCCAGGCCTGGTAGTG
             GCTAGGGCCAGGAGGGTGGGGTTGGTGGGAAGCAGTCAGATCCCAAAGAGATTTGGGGAT
             TGGAAGCAAAAGGATTTGCTGGTGACTTGCACATGGGAGGGAGAGAGGTCAGTGCCTCTG
             [T,C]
             TAATCAAGGAATCCAGATTGCCACCGAAATTTCTAGGCCCGAGATATTTAGGTAGTGTCT
             CACTCTGTCACCCAGGATGGAGTGCAGTGGCGCCATCTCGGCTCACTGTAACCTCCGCCT
             CCCAGGTTTAAACGATTCTCCCACCTCAGCCTCCTGAGTAGCTGGGATTACAGGCATGTG
             CCACCACTCCCGGCTAATTTTTGTATTTTTAGTAGAGACGGGGTTTCACCACGTTGGCCA
             GGCTGGTCTTGAACTCCTGACCTCAAGTGATCCACCCACGACAGCCTCCCAAAGTGCTGG

7741    CCTGATGACCTCAAGCTCCCCACGGACAACCAGTGAGTGAACTTTTCACCCTGCCAGGTG
             GGAGAGGGAAGGAGGGGTGGGACTTTCTGTGTTTTGCAGATGAGGAAACCAAGGCTCAGA
             GAGGGAAAGCCACCTTCCCAGAGCCACACAGCCAGAAAGAGGAGGCAAATTCCACCTCCG
             GCCCCTGTGACCCCGCCAAGCCTCCACCTTAATCTTTCACACCTCAGGGCACTGGGGGAA
             GCACTCGGGGCTGGAGGTTCAAAGTCCTGGGTCCTCATCCTGACATTATGGCCACCTGGC
             [C,T]
             ATGGGACCTGGAGCCAGTCACCACTGCTCTCTGAATGCAGGTTCTCCATTTCTATAATGG
             GCAGTGAGGATCAGATGAAGCATTGGGTGTCTTGCGGAGCCCCCCAGAAGGATGTGGGGT
             TGATGCCTCTGCTAAGTGCTGAGCATGTCTGGGGTCTCCTGTACCCAGGACCCTGTGTGG
```

FIGURE 3K

```
         AAGGCACCTGAGAGGCTGAGGGAGCTCCAGGCAGGCTGGGGAAGTCCCCTTCTCCACTCC
         TCTCTGGTCACTGAAGCTCGAAGTGGGGAGCATGAGGACAGGACGTTACCCCTTGTCAAG

8294   GAAGCTCGAAGTGGGGAGCATGAGGACAGGACGTTACCCCTTGTCAAGGCACCCAGGCTG
         CCAAGACAGAGACAAGCAGCATTGCTCCGGCCAGCACTTATTGACGCTTGAAGGTGTCCC
         CTGGCCCAAGGAAGGGCAGTTATCATCAGCCCGGGAGGCGGGGGAAGGATGGACTCTGCA
         GTGGGGTCCGCTCCTCATTGCCTGCTCTCTCAGGGCTCCAGAAGGAGGAAGAGGCCGGGC
         ACAGTGGCTCACACCTATAATCCCAGCACTTTTGGAAGGTCGAGGTGGGCAGATCACCTGA
         [A,G]
         GTTGGGAGTTTGAGACCAGCCTGGCCAACATGGTGAAACCCCATCTCTACCAAAAATATA
         AAAATTTAGTCAGGCATGGTGGTGTGCGCTTGTAATCCCAGCTACTTGGGAGGCCGAGGC
         AGGAGAATCGCTTGAACCCGGGAGGCAGAGGTTGCAGTGAGCTGAGACTGCGCCACTGCA
         CTCCAGCCTGGGTGACAGAGCGAGACTCTGTCTAAGAAAAAAAAAAGAAAAGAAGAAAGA
         AGATGGCCTGGGAGCCCGCAAGAGCATTTTCCAGGCTTAGGGCATCCTTTGGGTCTGCAG

9313   TGGGCCGGGTGCGGTTGCTCATGCCTGTAATCCCAGCAGTTTGGGAGGCCGAGGCAGGTG
         GATCACTTGAGGTCAGGAGTTTGAGACCAGCCTGGCCAACATGGAGAAACCCTGTCTCTA
         CTAAAAATCCAAATTAGCCAGGCGTGGTGACAGGTGCCTGTAGTCCCAGCCACTTGGGAG
         GCTGAGGCAGGAGAATTGCTTGAACCCGGAAGACGGAGTTTGCAGTGAGCCGAGATCGTG
         CCACTGCACTCCAGCCTGGGCAGCAGAGCCAGACTCCATCTCAAAAAAAAAAAAAAAAAA
         [A,-,G]
         AAGAATTGGGTCTTTGGAAGGTCCCTGGAGACTGAAAGGAGCCCTTTGCAGGTGGCAGTG
         CAGAGACCAGCGCAGACCCTTGCTACTGGCAGCCGGGGGAGTGTTTGCGGCTGAATGAAT
         GAACAGGTTTTGGAGGGCAGCGTGGCCTTCAGAGGCGATGCAGGGCTGTGGCAGTTTCTA
         ATACTTATTGCACAGTCACTGCTAATAACAATAATAATAATAATACCTAACATTAATGGA
         GTGCTTACTCTGTGCCAGCCACTATTTTGTTTTTGTTGTTTTCAGTGACAGGGTCTCGCT

10838   CTGTACTCTAGCCTGGGCAACAGAGCAAGACTCTGTCTCCAAAAAAGAAAATAAAGTTGG
         GAAAGGCTCACTAACTTCATCAGATGAGAACAA
         [G,A]
         GACATGTTTGAAGTGTGAGGCCGAAGCCTGGAGAACGCTATGCGCCCAGGAAATGCAGGG
         CAGCAGAGACTCAAGATGCCAGCGCCTGTTCTG

11093   AAATAAAGTTGGGAAAGGCTCACTAACTTCATCAGATGAGAACAAAGACATGTTTGAAGT
         GTGAGGCCGAAGCCTGGAGAACGCTATGCGCCCAGGAAATGCAGGGCAGCAGAGACTCAA
         GATGCCAGCGCCTGTTCTGGAGGCCCAGATGGGCCCTGCAATGCCCACTCACCCTGCCCT
         CCCTCTTGCCCCAGACATCACCGGCCCCATCATCCTGCAGACGTACCGCGCCATTGCCGA
         CTACGAGAAGACCTCGGGCTCCGAGATGGCTCTGTCCACGGGGGACGTGGTGGAGGTCGT
         [G,A]
         GAGAAGAGCGAGAGCGGTCAGACCTCCCACCTTACGGGGCTCCTTCCCCTGGTGCTCAGG
         AACCCACAGCCACAAGCCCCCTGCCAAGGCTCAGGCAGCCTGGCCCCTGGGAGGACTCCA
         GCTCTGTTAGGGGCCCTAAATGTCCTCCCCACACTGTGGGTCGCCTTCTCTCTTAGTGTG
         CACCCTGTGGTGGCTGTGGGCATCTGTGCATGGCAGGCCGGGCGGGGCATGTCTGCGTG
         TTCTGTCTGGATGGGTATGGGACCGTCTGTTCATTATGAAGTGGGCTCAGAGCTGTGATT

11195   AGGGCAGCAGAGACTCAAGATGCCAGCGCCTGTTCTGGAGGCCCAGATGGGCCCTGCAAT
         GCCCACTCACCCTGCCCTCCCTCTTGCCCCAGACATCACCGGCCCCATCATCCTGCAGAC
         GTACCGCGCCATTGCCGACTACGAGAAGACCTCGGGCTCCGAGATGGCTCTGTCCACGGG
         GGACGTGGTGGAGGTCGTGGAGAAGAGCGAGAGCGGTCAGACCTCCCACCTTACGGGGCT
         CCTTCCCCTGGTGCTCAGGAACCCACAGCCACAAGCCCCCTGCCAAGGCTCAGGCAGCCT
         [T,G]
         GCCCCTGGGAGGACTCCAGCTCTGTTAGGGGCCCTAAATGTCCTCCCCACACTGTGGGTC
         GCCTTCTCTCTTAGTGTGCACCCTGTGGTGGCTGTGGGCATCTGTGCATGGCAGGCCGGG
         GCGGGGCATGTCTGCGTGTTCTGTCTGGATGGGTATGGGACCGTCTGTTCATTATGAAGT
         GGGCTCAGAGCTGTGATTCTGTGAGCATGTGTGCATGCATGCATGTGACCTCATTGTCCA
         GTGTGGTGAAGGTGACATTTCCAAATCTGAGCATTGGACATCAGTGTGTCTGTGTCCCTG

11213   GATGCCAGCGCCTGTTCTGGAGGCCCAGATGGGCCCTGCAATGCCCACTCACCCTGCCCT
         CCCTCTTGCCCCAGACATCACCGGCCCCATCATCCTGCAGACGTACCGCGCCATTGCCGA
         CTACGAGAAGACCTCGGGCTCCGAGATGGCTCTGTCCACGGGGGACGTGGTGGAGGTCGT
         GGAGAAGAGCGAGAGCGGTCAGACCTCCCACCTTACGGGGCTCCTTCCCCTGGTGCTCAG
         GAACCCACAGCCACAAGCCCCCTGCCAAGGCTCAGGCAGCCTGGCCCCTGGGAGGACTCC
         [G,A]
         GCTCTGTTAGGGGCCCTAAATGTCCTCCCCACACTGTGGGTCGCCTTCTCTCTTAGTGTG
         CACCCTGTGGTGGCTGTGGGCATCTGTGCATGGCAGGCCGGGCGGGGCATGTCTGCGTG
```

FIGURE 3L

```
        TTCTGTCTGGATGGGTATGGGACCGTCTGTTCATTATGAAGTGGGCTCAGAGCTGTGATT
        CTGTGAGCATGTGTGCATGCATGCATGTGACCTCATTGTCCAGTGTGGTGAAGGTGACAT
        TTCCAAATCTGAGCATTGGACATCAGTGTGTCTGTGTCCCTGTGTCCTCACCATCCCTGA

11263   ACCCTGCCCTCCCTCTTGCCCCAGACATCACCGGCCCCATCATCCTGCAGACGTACCGCG
        CCATTGCCGACTACGAGAAGACCTCGGGCTCCGAGATGGCTCTGTCCACGGGGGACGTGG
        TGGAGGTCGTGGAGAAGAGCGAGAGCGGTCAGACCTCCCACCTTACGGGGCTCCTTCCCC
        TGGTGCTCAGGAACCCACAGCCACAAGCCCCTGCCAAGGCTCAGGCAGCCTGGCCCCTG
        GGAGGACTCCAGCTCTGTTAGGGGCCCTAAATGTCCTCCCCACACTGTGGGTCGCCTTCT
        [C,G]
        TCTTAGTGTGCACCCTGTGGTGGCTGTGGGCATCTGTGCATGGCAGGCCGGGGCGGGGCA
        TGTCTGCGTGTTCTGTCTGGATGGGTATGGGACCGTCTGTTCATTATGAAGTGGGCTCAG
        AGCTGTGATTCTGTGAGCATGTGTGCATGCATGCATGTGACCTCATTGTCCAGTGTGGTG
        AAGGTGACATTTCCAAATCTGAGCATTGGACATCAGTGTGTCTGTGTCCCTGTGTCCTCA
        CCATCCCTGATGGCTGCAGGGAGCCGCTGGGCCCTGCCCCTCAGTCACATTCCCGCACCT

13707   GGGGTGTTTAGGGATCTGGGGTGACTTGTCCCTGGGACTCTGGGTAAGCCACTGCCCCTC
        TCTGGGCTTAGTTTCCATCTCAGTAGCAGGGAGGGATGAGCCCACCCTTGCCTGTCTTGT
        GGGGATCCAATGTCCTTGTCCAAGTGGGTGCATTTCTCCTTTGTGATTTAGGGTCTCTTC
        CCAACCATCTATTATTATTCCTTCTCTGGCAACATGGTGAACTGTTGTATAAATAATTAC
        ATTCCTAGCTAGGCGCAATGGCCCAGGCCTGTAATCCCAGCACTTTGGGAGCCCAGGACA
        [G,A]
        GACGATCACGTGAGGTCAGGAGTTCGAGACCACCCTGGCCAACATGGCAAAACCCTATCT
        CTACTAAAAACACAAACATGAGCCGGGTGTTGTGGTGGGAGCCTGTAATCCCAGCTACTC
        GGGAGTCTGAGACAAGAGAATCACTTCAACCCGGGAGGCGGAGGTTGCAGTGAGCCAAGA
        TCGCGCCATTGCACTCCAGCCTGGGCAACGAGAGCGAAACTCCGTCTCAAAAAAAAAAAA
        AAAAAAAAAGATTACTTTCTTTTTATCATTCCTTTATCTTTTAAAGCTTTCTTGCAGTCA

14629   TGTTTATCCTCCAAATGAATGCAGAAATACTAATTATCTTTTTTCTGGTTCTGGGGAACA
        CAGAATTCTAGCGGCTTGTGGAGCCATTTCCCTGGAGCCATGGGGCCTCCCAGGTCCTTT
        CCTGTGTCTTCATTTTTTACGAATTTTTTCATTTTTTGAGACAGGATCTTGCTCTGACTC
        CCAGGCTGGAGCACAATCATCGCTCACTCAAGCGATCCTCCCACCTCAGGCTCCCACGTA
        GCTGGGACTACAGGTGAGCACCACCACATCTGGCTAATGTTTTTTAATTTTTTTTGTAGGG
        [G,A]
        TGGGGTCTCACTATGGTGCCAAGACTAGTCTTAAACTCCTGGCCTCAAGAGTTCCTCCTG
        CCTTGGCCTCCCAAAGCACTGGGATTACAGGAATGAGCCTCCATGCTGGGCCTTTGCTGG
        CGTCTTCAGAGCCCTAGGTCACAGGGCCAGCCTGGCGCCCTGCCGCAAGCTTATCTTAAA
        GCTGGGACCACAACATGCATACCTGCAGCCGGGCCCGGGGCCAGAGGGCTTTGAGGCAGC
        ATTTCTCAGCCTTTTAGACACACACTCTGTTAACCCCCATCCTGTGTCTCTGATAATCTT

14698   TTCATTTTTTACGAATTTTTTCATTTTTTGAGACAGGATCTTGCTCTGACTCCCAGGCTG
        GAGCACAATCATCGCTCACTCAAGCGATCCTCCCACCTCAGGCTCCCACGTAGCTGGGAC
        TACAGGTGAGCACCACCACATCTGGCTAATGTTTTTTAATTTTTTTTGTAGGGGTGGGGTC
        TCACTATGGTGCCAAGACTAGTCTTAAACTCCTGGCCTCAAGAGTTCCTCCTGCCTTGGC
        C
        [T,A]
        CCCAAAGCACTGGGATTACAGGAATGAGCCTCCATGCTGGGCCTTTGCTGGCGTCTTCAG
        AGCCCTAGGTCACAGGGCCAGCCTGGCGCCCTGCCGCAAGCTTATCTTAAAGCTGGGACC
        ACAACATGCATACCTGCAGCCGGGCCCGGGGCCAGAGGGCTTTGAGGCAGCATTTCTCAG
        CCTTTTAGACACACACTCTGTTAACCCCCATCCTGTGTCTCTGATAATCTTCTTGTGATC
        C

16095   AATACCTGTCCCCTGCGGTGACCTGGATCTGCTAACCTCCACCCCTGCCTAGACTGTGGA
        AGGATTGCTGGAAGGGTCTCAGTTGCACAGACCAGGAAACTGAGGCCCACAGAGGCAGGT
        GTCCGGTTGTTTGCAACCTCTCAGCCTGTGCTAACCCCAATTGTTCAGAGAGAGCCCTGA
        AACCCTCTCCTCTGGGCGCCCCAGGTGACTGCCCCAGCCTCAAGGGCTGCCTCTGTTGC
        AGGAAAGACGACGTCACAGGCTACTTCCCGTCCATGTACCTGCAAAAGTCAGGGCAAGAC
        [C,T,G]
        TGTCCCAGGCCCAACGCCAGATCAAGCGGGGGGCGCCGCCCCGCAGGTAAGCGGGGGTCC
        CCGGGGCTGGCGGGGTCGAGCGGGGCGCACCACGGGTTCGCTCTGTCTAGGCCATAGCT
        TGGCAGTGCCGGGGCGGGGCTCTCAGCCTGGCAGGAGAGGCAGGACCCTCACGGGGGAA
        AGGGGCTGGACGCGCCTGGCCGCGGTGTGGGCTGGCACGGGGCGGAAGGAAAGCGGCG
        ATGCCCGGGGGCTTTGGGGATGGGCAGTCCAGGGGGGCTCCCCGGAGAGGGGGACGACAG

16266   GAGCCCTGAAACCCTCTCCTCTGGGCGCCCCAGGTGACTGCCCCAGCCTCAAGGGCTGC
```

FIGURE 3M

```
         CTCTGTTGCAGGAAAGACGACGTCACAGGCTACTTCCCGTCCATGTACCTGCAAAAGTCA
         GGGCAAGACGTGTCCCAGGCCCAACGCCAGATCAAGCGGGGGGCGCCGCCCCGCAGGTAA
         GCGGGGGTCCCCGGGGCTGGGCGGGGTCGAGCGGGGCGCACCACGGGTTCGCTCTGTCTA
         GGCCATAGCTTGGCAGTGCCGGGGCGGGGGCTCTCAGCCTGGCAGGAGAGGCAGGACCCT
         [C,T]
         ACGGGGGAAAGGGGCTGGACGCGCCTGGCCGCGGTGTGGGGCTGGCACGGGGCGGAAGG
         AAAGCGGCGATGCCCGGGGGCTTTGGGGATGGGCAGTCCAGGGGGGCTCCCCGGAGAGGG
         GGACGACAGACCGAAGGCTGGTGAGGGGCGTGGAAAACCGCCCAGGCTCTGCTGCAGGGC
         AAGGGTCCTTGTCGTGACGGGGGCAGCCGCCTCTTGTCCCGCCGGGGTCGTGCAGACTAC
         CGGCCCCCTACTGCCCCCCACTTCCTCGGACCAGGGGTGCCCATCTGAGTCCCTGGGGGC

16629   AGCGGCGATGCCCGGGGGCTTTGGGGATGGGCAGTCCAGGGGGGCTCCCCGGAGAGGGGG
         ACGACAGACCGAAGGCTGGTGAGGGGCGTGGAAAACCGCCCAGGCTCTGCTGCAGGGCAA
         GGGTCCTTGTCGTGACGGGGGCAGCCGCCTCTTGTCCCGCCGGGGTCGTGCAGACTACCG
         GCCCCCTACTGCCCCCCACTTCCTCGGACCAGGGGTGCCCATCTGAGTCCCTGGGGGCAG
         GGGCGCCCTCGGGCTTTGACGACGCCCCGTCCCGCTGGGCCAGGTCGTCCATCCGCAACG
         [C,T]
         GCACAGCATCCACCAGCGGTCGCGGAAGCGCCTCAGCCAGGACGCCTATCGCCGCAACAG
         CGTCCGTTTTCTGCAGCAGCGACGCCGCCAGGCGCGGCCGGGACCGCAGAGCCCCGGGAG
         CCCGCTCGGTGAGTGCAGCGGGAGAGGGCAGGAAGGGCAAGCCCTAGGGGCGGAGTCAGC
         GGGAGAGGCGGGGCCAGAGGCAGGGCCAGAGTAGCGGGGCGGGACCAGAGGGCGGAATCA
         GAGGGAGAGGCGGGGACTGGAGGCGGGGGCAGAGGAGGAGCCAGCGCTAGGGGCGGAGC

16642   GGGGGCTTTGGGGATGGGCAGTCCAGGGGGGCTCCCCGGAGAGGGGGACGACAGACCGAA
         GGCTGGTGAGGGGCGTGGAAAACCGCCCAGGCTCTGCTGCAGGGCAAGGGTCCTTGTCGT
         GACGGGGGCAGCCGCCTCTTGTCCCGCCGGGGTCGTGCAGACTACCGGCCCCCTACTGCC
         CCCCACTTCCTCGGACCAGGGGTGCCCATCTGAGTCCCTGGGGGCAGGGGCGCCCTCGGG
         CTTTGACGACGCCCCGTCCCGCTGGGCCAGGTCGTCCATCCGCAACGCGCACAGCATCCA
         [C,T]
         CAGCGGTCGCGGAAGCGCCTCAGCCAGGACGCCTATCGCCGCAACAGCGTCCGTTTTCTG
         CAGCAGCGACGCCGCCAGGCGCGGCCGGGACCGCAGAGCCCCGGGAGCCCGCTCGGTGAG
         TGCAGCGGGAGAGGGCAGGAAGGGCAAGCCCTAGGGGCGGAGTCAGCGGGAGAGGCGGGG
         CCAGAGGCAGGGCCAGAGTAGCGGGGCGGGACCAGAGGGCGGAATCAGAGGGAGAGGCGG
         GGACTGGAGGCGGGGGCAGAGGAGGAGCCAGCGCTAGGGGCGGAGCGATCCCTAAGAGG

18537   AAAAAAGTAACTTAGGTGCAGGGTGTCCTCTGTTATTCACTGAGACCGTGCCCCGGTTAT
         GAGGTTGTACCAGAAAGCAAGTATTCACTATGCACACTATTCACCGCTCACCCTAGCATT
         GAAGCCAGCCTGTAGCCTGAAAGCCTTTGCTTTGAGGGCAGGTCTTTCCCCAAAATGCAG
         ACACGAAGGTGCAAAGTGAAGCTGCCAGTCTTGCAAAAGATGTAACTTGTCACGAAGGCC
         ACGAGTGGCAGGGAGAGCTGTCCCACATTTGCGGAAGTGGCTATGTGAGGACGGGGGAGG
         [C,T]
         GGGTCCCTTAGAGATAAGAGACAATCATAAGGGGAGATATCAGAGAAAATCGTAAGGGGA
         GCAGATGGTTGTCAAGAGAATAGGCTGACCATCGAAGGACTGGCAGAAGCTTTCAGAAAA
         CCACTGGACGGCTGGGCACAGTGGCTTAGGCCTGTAATCCCAGCACTTTGGGAGGCTGAC
         GCAGGTGAATCACTTGAGGTCAGGAGTTCCAGACCAGCCTGGCCAACATGGTGAAACCCC
         ATCTCTACAGAAAATATAAAAATTAGCCAGGCGTGGTGGCACAAGCCTAGAATCCCAGCT

18589   CCGGTTATGAGGTTGTACCAGAAAGCAAGTATTCACTATGCACACTATTCACCGCTCACC
         CTAGCATTGAAGCCAGCCTGTAGCCTGAAAGCCTTTGCTTTGAGGGCAGGTCTTTCCCCA
         AAATGCAGACACGAAGGTGCAAAGTGAAGCTGCCAGTCTTGCAAAAGATGTAACTTGTCA
         CGAAGGCCACGAGTGGCAGGGAGAGCTGTCCCACATTTGCGGAAGTGGCTATGTGAGGAC
         GGGGGAGGCGGGTCCCTTAGAGATAAGAGACAATCATAAGGGGAGATATCAGAGAAAATC
         [G,A]
         TAAGGGGAGCAGATGGTTGTCAAGAGAATAGGCTGACCATCGAAGGACTGGCAGAAGCTT
         TCAGAAAACCACTGGACGGCTGGGCACAGTGGCTTAGGCCTGTAATCCCAGCACTTTGGG
         AGGCTGACGCAGGTGAATCACTTGAGGTCAGGAGTTCCAGACCAGCCTGGCCAACATGGT
         GAAACCCCATCTCTACAGAAAATATAAAAATTAGCCAGGCGTGGTGGCACAAGCCTAGAA
         TCCCAGCTACTTGGGAGGCTGAGG

18720   CGAAGGTGCAAAGTGAAGCTGCCAGTCTTGCAAAAGATGTAACTTGTCACGAAGGCCACG
         AGTGGCAGGGAGAGCTGTCCCACATTTGCGGAAGTGGCTATGTGAGGACGGGGAGGCGG
         GTCCCTTAGAGATAAGAGACAATCATAAGGGGAGATATCAGAGAAAATCGTAAGGGGAGC
         AGATGGTTGTCAAGAGAATAGGCTGACCATCGAAGGACTGGCAGAAGCTTTCAGAAAACC
         ACTGGACGGCTGGGCACAGTGGCTTAGGCCTGTAATCCCAGCACTTTGGGAGGCTGACGC
         [G,A]
```

FIGURE 3N

```
         GGTGAATCACTTGAGGTCAGGAGTTCCAGACCAGCCTGGCCAACATGGTGAAACCCCATC
         TCTACAGAAAATATAAAAATTAGCCAGGCGTGGTGGCACAAGCCTAGAATCCCAGCTACT
         TGGGAGGCTGAGG

18782    TGGCAGGGAGAGCTGTCCCACATTTGCGGAAGTGGCTATGTGAGGACGGGGGAGGCGGGT
         CCCTTAGAGATAAGAGACAATCATAAGGGGAGATATCAGAGAAAATCGTAAGGGGAGCAG
         ATGGTTGTCAAGAGAATAGGCTGACCATCGAAGGACTGGCAGAAGCTTTCAGAAAACCAC
         TGGACGGCTGGGCACAGTGGCTTAGGCCTGTAATCCCAGCACTTTGGGAGGCTGACGCAG
         GTGAATCACTTGAGGTCAGGAGTTCCAGACCAGCCTGGCCAACATGGTGAAACCCCATCT
         [C,T]
         TACAGAAAATATAAAAATTAGCCAGGCGTGGTGGCACAAGCCTAGAATCCCAGCTACTTG
         GGAGGCTGAGG

18841    TCCCTTAGAGATAAGAGACAATCATAAGGGGAGATATCAGAGAAAATCGTAAGGGGAGCA
         GATGGTTGTCAAGAGAATAGGCTGACCATCGAAGGACTGGCAGAAGCTTTCAGAAAACCA
         CTGGACGGCTGGGCACAGTGGCTTAGGCCTGTAATCCCAGCACTTTGGGAGGCTGACGCA
         GGTGAATCACTTGAGGTCAGGAGTTCCAGACCAGCCTGGCCAACATGGTGAAACCCCATC
         TCTACAGAAAATATAAAAATTAGCCAGGCGTGGTGGCACAAGCCTAGAATCCCAGCTACT
         [C,T]
         GGGAGGCTGAGG
```

Chromosome mapping
Chromosome 19

FIGURE 3O

SEQUENCE LISTING

<160> NUMBER OF SEQ ID NOS: 4

<210> SEQ ID NO 1
<211> LENGTH: 1382
<212> TYPE: DNA
<213> ORGANISM: Homo sapien

<400> SEQUENCE: 1

| | | | | | | |
|---|---|---|---|---|---|---|
| cctggaagtg | ccagggagca | ctggaggcca | cccagtcatg | ggggacacct | tcatccgtca | 60 |
| catcgccctg | ctgggctttg | agaagcgctt | cgtacccagc | cagcactatg | tgtacatgtt | 120 |
| cctggtgaaa | tggcaggacc | tgtcggagaa | ggtggtctac | cggcgcttca | ccgagatcta | 180 |
| cgagttccat | aaaaccttaa | aagaaatgtt | ccctattgag | gcaggggcga | tcaatccaga | 240 |
| gaacaggatc | atccccacc | tcccagctcc | caagtggttt | gacgggcagc | gggccgccga | 300 |
| gaaccgccag | ggcacactta | ccgagtactg | cagcacgctc | atgagcctgc | ccaccaagat | 360 |
| ctcccgctgt | ccccacctcc | tcgacttctt | caaggtgcgc | cctgatgacc | tcaagctccc | 420 |
| cacggacaac | cagacaaaaa | agccagagac | atacttgatg | cccaaagatg | gcaagagtac | 480 |
| cgcgacagac | atcaccggcc | ccatcatcct | gcagacgtac | cgcgccattg | ccaactacga | 540 |
| gaagacctcg | ggctccgaga | tggctctgtc | cacgggggac | gtggtggagg | tcgtagaaa | 600 |
| gagcgagagc | ggttggtggt | tctgtcagat | gaaagcaaag | cgaggctgga | tcccagcgtc | 660 |

-continued

```
cttcctcgag cccctggaca gtcctgacga gacggaagac cctgagccca actatgcagg    720
tgagccatac gtcgccatca aggcctacac tgctgtggag ggggacgagg tgtccctgct    780
cgagggtgaa gctgttgagg tcattcacaa gctcctggac ggctggaaag acgacgtcac    840
aggctacttc ccgtccatgt acctgcaaaa gtcagggcaa gacgtgtccc aggcccaacg    900
ccagatcaag cggggggcgc cgccccgcag gtcgtccatc cgcaacgcgc acagcatcca    960
ccagcggtcg cggaagcgcc tcagccagga cgcctatcgc cgcaacagcg tccgttttct   1020
gcagcagcga cgccgccagg cgcggccggg accgcagagc cccgggagcc cgctcgagga   1080
ggagcggcag acgcagcgct ctaaaccgca gccggcggtg ccccgcggc cgagcgccga    1140 cctcatcctg aaccgctgca gcgagagcac caagcggaag ctggcgtctg ccgtctgagg   1200
ctggagcgca gtccccagct agcgtctcgg cccttgccgc ccgtgcctg tatatacgtg    1260 ttctatagag cctggcgtct ggacgccgag ggcagcccg acccctgtcc agcgcggctc    1320
ccgccaccct caataaatgt tgcttggagt ggaaaaaaaa aaaaaaaaa aaaaaaaaa    1380 aa                                                                 1382
```

<210> SEQ ID NO 2
<211> LENGTH: 386
<212> TYPE: PRT
<213> ORGANISM: Homo sapien

<400> SEQUENCE: 2

```
Met Gly Asp Thr Phe Ile Arg His Ile Ala Leu Leu Gly Phe Glu Lys
 1               5                  10                  15

Arg Phe Val Pro Ser Gln His Tyr Val Tyr Met Phe Leu Val Lys Trp
                20                  25                  30

Gln Asp Leu Ser Glu Lys Val Val Tyr Arg Arg Phe Thr Glu Ile Tyr
            35                  40                  45

Glu Phe His Lys Thr Leu Lys Glu Met Phe Pro Ile Glu Ala Gly Ala
        50                  55                  60

Ile Asn Pro Glu Asn Arg Ile Pro His Leu Pro Ala Pro Lys Trp
 65                  70                  75                  80

Phe Asp Gly Gln Arg Ala Ala Glu Asn Arg Gln Gly Thr Leu Thr Glu
                85                  90                  95

Tyr Cys Ser Thr Leu Met Ser Leu Pro Thr Lys Ile Ser Arg Cys Pro
            100                 105                 110

His Leu Leu Asp Phe Phe Lys Val Arg Pro Asp Asp Leu Lys Leu Pro
        115                 120                 125

Thr Asp Asn Gln Thr Lys Lys Pro Glu Thr Tyr Leu Met Pro Lys Asp
    130                 135                 140

Gly Lys Ser Thr Ala Thr Asp Ile Thr Gly Pro Ile Ile Leu Gln Thr
145                 150                 155                 160

Tyr Arg Ala Ile Ala Asn Tyr Glu Lys Thr Ser Gly Ser Glu Met Ala
                165                 170                 175

Leu Ser Thr Gly Asp Val Val Glu Val Val Glu Lys Ser Glu Ser Gly
            180                 185                 190

Trp Trp Phe Cys Gln Met Lys Ala Lys Arg Gly Trp Ile Pro Ala Ser
        195                 200                 205

Phe Leu Glu Pro Leu Asp Ser Pro Asp Glu Thr Glu Asp Pro Glu Pro
    210                 215                 220

Asn Tyr Ala Gly Glu Pro Tyr Val Ala Ile Lys Ala Tyr Thr Ala Val
225                 230                 235                 240
```

```
Glu Gly Asp Glu Val Ser Leu Leu Glu Gly Glu Ala Val Glu Val Ile
                245                 250                 255

His Lys Leu Leu Asp Gly Trp Lys Asp Asp Val Thr Gly Tyr Phe Pro
            260                 265                 270

Ser Met Tyr Leu Gln Lys Ser Gly Gln Asp Val Ser Gln Ala Gln Arg
        275                 280                 285

Gln Ile Lys Arg Gly Ala Pro Pro Arg Ser Ser Ile Arg Asn Ala
    290                 295                 300

His Ser Ile His Gln Arg Ser Arg Lys Arg Leu Ser Gln Asp Ala Tyr
305                 310                 315                 320

Arg Arg Asn Ser Val Arg Phe Leu Gln Gln Arg Arg Gln Ala Arg
                325                 330                 335

Pro Gly Pro Gln Ser Pro Gly Ser Pro Leu Glu Glu Glu Arg Gln Thr
            340                 345                 350

Gln Arg Ser Lys Pro Gln Pro Ala Val Pro Pro Arg Pro Ser Ala Asp
        355                 360                 365

Leu Ile Leu Asn Arg Cys Ser Glu Ser Thr Lys Arg Lys Leu Ala Ser
    370                 375                 380

Ala Val
385

<210> SEQ ID NO 3
<211> LENGTH: 18853
<212> TYPE: DNA
<213> ORGANISM: Homo sapien
<220> FEATURE:
<221> NAME/KEY: misc_feature
<222> LOCATION: (1)...(18853)
<223> OTHER INFORMATION: n = A,T,C or G

<400> SEQUENCE: 3
tactaaaaat acaaaattag ccaggcgtgg tggcgcacac ctgtaatccc agctacttgg      60
gaagctgagg caggagaatc gcttgaacct ggaaggcaga ggttgcagtg agccgagatt     120
gtgccactgc actccagcct gggcaacaag agcgaaactt cgcttcaaac aaataaatta     180
acgcccagca tgtcttggct ttcatctgcc agacctcaac cctcaccccc aggagatcag     240
gtccggacca tgagctgacc ctggactcag gcaagggtga gttggtgcag ccctggcctg     300
ctgggaggca caggctgcag caggctgcct ggggctgagg cccgccactc atgaactcat     360
gaccttgaat gagctccaaa agctctgggc ctcccaggct ctaggggag tgggagagag      420 aggcctcagc ctgtccctgg gcatgctgcc cctcctcac ctctttgtcc caaatcccct      480
tcctggcaaa gctgacagtc ttaatatcac tctggagaaa actgagtcag ccctaaggaa     540
caattcaatg aaccatttgc ttacttgagg attggaactc aagtctcact caaagtctgt     600
gccattttcg tcccagctgt cactggccct catccacaca cacccaagga tgagcatcta     660
acgcttgcat gcacactccc atgcccgcgt tcattcactc attcattcat tcattcactc     720
attcattgac tcattcattc attcactcac tcattcattc actcagtgaa tgttgcagtc     780
acgatccaaa tatttatggc ctctgtgtgc caggcactag atggagggc tggggctaga      840 gccctgata acccggtcat gccctagctt tcctgggaca cacattgtgg taaggggaga      900
ctaaaaaaat taagtcaggc caggcacggt ggctcatgcc tgaatcccag cactttggga     960
ggccgaggcg agtgaattac ctgaggtcag gagttcaaga ccagcctggc caacatggag    1020
aaacccagtc tctaattaaa aaaaaaaaa aaattagcca ggtgtggtgg cacatgcctg    1080
taatcccagc tactcaggag actaacgcaa gagaattgct tgaacccagg aggcagaggt    1140
```

```
tgcggtgagc cgagatcgcg ccattgcact ccagcctggg aaacaagagc gagactccat   1200
ctcaaaaaaa aaaaaagtgg gaggcagagg caggaggatc actagaggcc agtagtttga   1260
gaccatcctg gcaacatag caggaccctg tctgtacaaa aaaattaaaa aaaatttaac   1320
cgggcatggt ggcacacacc cgtagtccca gctactccag aggctgaggc aggaggatcg   1380
ctggagccca ggagttggag gctgcagtga actgtgatcc caccactgca cttaagcctg   1440
gataacaaag caagaccctg tctcaaataa caatagcaat aataataaag aaaaattaaa   1500
tgcaatttgc gatgcatcag tgataagtgc tctgcagaaa aaggaggcag aagaggctg    1560 agaaaggtat gaggtttgct atgcaatgtg aagttatcaa ggaaggcttc tcggaagagg   1620
tgacatttga gcagagaaat ggaggagagt tatggaggga agatggtgaa tgggggaac   1680 atggtcaaga ccaggaatat ggtcaagggg ggaaagatgg tcaagggac gcagcaaatg    1740 caaaggccct gaggcaggag cagcttgatt acccccaaa acccgtgggg cccgtgcagg    1800
cgacgggaag gacaagtgta aacccttttc cttgtccctg caggtgtgtg tgaacatgag   1860
tctgcccatg tttacaccct gcaagcctga agagtcccca gaaactgaaa gaagaagcaa   1920
agcccttcct gtaccctccc tgcccctgt cccgaccgcg acaaaagcga cttcctcttt    1980
ccagtgcatt taaggcgcag cctggaagtg ccagggagca ctggaggcca cccagtcatg   2040
ggggacacct tcatccgtca catcgccctg ctgggctttg agaagcgctt cgtacccagc   2100
cagcactatg tgagtagctg gtggagggca tcccgtgggg ggaatacggg agggacagca   2160
cggccaccct tgcagtccca gggccaacca gctccagtga ggactaacgg ggcagggtct   2220
tgggcacctg gtccctggtc tttgagcctg gatctacccc tctgatccct gggaagacag   2280
ttcccttgga cccgccctgg gccccagccc tttactgtcc ccgcctgtgt ccccagccag   2340
gccctcagcc ttagccagga gtcctctttc tgctcccctg ccatggccag gcagcccagc   2400
gctctctcag gtccgaggcc cactcctcca ggaagcttc cctgactagc ccagctatca   2460
gagagtggcc ctcccaagag ggaggcctgg aaactaaagc tctctctctc cccagctgcc   2520
tgtagtgtca gttagagtct tatcctctcc agtagggtga caccatgaca ggggccaata   2580
gagtcctccc atctgtcccc aaggaggctg gacaaatgcc tgctcagaca cacaagtcca   2640
ctgggtcccc taatcccata ggaaggccag ggaggaacta catttaggaa attgaagctt   2700
gtatggaaca tttagtccta tgtgccaaga cctttctctt ttttgttatt tttttgtgtt   2760
ttgagacaga gtcttgatct gttgcccagg ccagagtgca gtggcacgat ctcagctcac   2820
tgcaacctcc gccttccagg ttcaactggt tctcctgcct cagcctccag agtagttggg   2880
attacaggtg cccaccacca cgcctggcta ttttttgtat ttttagtaga cagggtttc    2940 caccatgttg gccagactgg tctcaaactc ctgacctcaa gtgatccacc cacctgggcc   3000
tcccaaagtg ctgggattac aggcatgagc caccgtgcct ggcctgtttt ttgaaatga    3060 ggtctggagt gcagtggtgc gatcatagtt cactgcagcc tcaacctccc aggcccaagt   3120
gatcctcctg cctcagcccc ttgagtagct ggggctacag cgcacacca ccatgcctgg    3180 ctagttttta aaatttttgt ggagatgagg tttcactatg ttgtccaggc taatcttgaa   3240
ctcctcggct taagcaaccc tctggtctca gcctcccaca gtgctaggat tacaagcgtg   3300
agctaccgtg cctagtcact tttctccttt tctttgtaac tttcagtttt gaaatttcaa   3360
atttacagaa aggctactgg gtgtcaaaac ggtaccagtc actccaatag tctttcactc   3420
accttcatcc acacctctct ttctgggat attttctgaa ttatttgaga gtgagttgaa    3480
gacgtgtttc tttacctcta aatactagtt gttgggcatt tcttaaaatc aaggcattct   3540
```

```
cttacataat cacaacacac gtgtcaaaat caggaaatta acatggacaa aacaccatta      3600
tccacccaca gactttactg aggtttcccc gattatcctg cttgtcctct gcagtgaaaa      3660
cttttttcag gtctaggatc cagtcaagga tcaatgtcat agcctttaac cttctttaat      3720
ctggatcagt ctttttttctt tttcttttttc tttttttgga cacggaatct cactctgtcg    3780
ccagactgga gtgcagtggt gcaatctcgg ctcattgcaa cctctgcctc ctgggttcaa      3840
gagattctcc tgcctcagcc tcctgagtag ctgggaatac aggtgcgcgc caccacgccc      3900
agctcgtttt tggtagagac agggttttgc cattgattct ggatcagtct ttttttttttt    3960 ttttatgaga tggagtctta ctctgtcacc caggctggag tgcaatggca caatctccac      4020
tcactgcatc ctccgcctcc caggttcaag caattctcgt gcctcagcct cccgagtagc      4080
tgggattaca ggcatgcgcc accatgcccg gctactttttt gtattttttag tagagacagg    4140 gtttcaccat gttagccagg ctgatctcga actcctgacg tcaggtgatc tgcccgcctc      4200
gacctcccaa agtgctggga ttacaggcgt gagccaccgt gccagcggat tctggatcgg      4260
tcttaatcag tctttgtctt ttgcaacttt gatgttttgc agagagcaga ccagttacct      4320
tgtagaatgt cccttagttt gggtttatct tcattagatt cagtttgtgt atccagggca      4380
gtggatctta gatgcaattc tgtcttcttt ttaattttttt tgagagggag tctcgctctg    4440
tcacccaggc tggagtgcag tggcacaacc tcagctcact gcagcctccg cctcccgggt      4500
tcaagcaatt ctcctgtccc agcctcccaa gtagctggga tcacaggtgc ccatcaccac      4560
taccgggtaa tttttgtgtt tttagtagag acagggtttc accatattgg tcaggctggt      4620
cttgaacgcc tgacctcagg tgatccacct gccttggcct cccaaagtgc tgggattaca      4680
gacgggagcc aacatgccca gccttcctgc ccctcccgtc ccctcccctc tcctcctgtc      4740
ccctcccttc ccctcccctta tcctcatgtc ccctcccttc ccctcccctc cccacccaag    4800
ctggagtgca gtggtgcaat catagctcac taaagccttg acctccaagt ctcaagcaat      4860
tctcctgcct cacctggggc acaggtgtg cggcaccaca cccggacaat ttttgtgttt      4920
ttagtagata tgggggtctc gctatgttgc ccaggctggt ctcaaactct tggactcaag      4980
cgatcttccc acctcggtac taaaaagtgc tgggattcca ggtgtgagcc accgtgccca      5040
gcctaggtcc tacttttatc tccaatttac agatgagtcc atttgagaga agctgacctt      5100
cttgccctgg gtctcaaggc tggggcgtgg cagcacttgg gtccacgttt gtgcccttc     5160 tgcaatccag gacaactgca agatggtcc tcacccaat cctctgggct tcctccagtg       5220
ggtagtggga tcctgggtgc acacagcaaa gcctctttgg aggctgaatg gggtcccccg      5280
actctggctt tccccaggt acatgttcct ggtgaaatgg caggacctgt cggagaaggt      5340
ggtctaccgg cgcttcaccg agatctacga gttccatgtg agtgtgggga cggaggaggg      5400
acagggaccc accgttccag ctccacccttt gggaaggac cttagcccag gtgatgggga      5460
aactgcagaa cccagaatcc cctcccagac cacagttaaa ggggatttat ttatttatat      5520
aaatttttgt gacagggtct tgctctgtca cccagggtct tgctctgtca ccactctgaa      5580
cacctcatgt tctctgatta caggcatgag cccccacggt cggccttttta ggtggttttg    5640 agaggtattt aggtttgcag tgcaggggcg caatcatagc tcactgcagc ctcaacctct      5700
ggggctcaag cgatcctcct gcctcagcct cctgagtagc tgggactata ggtgcgcatc      5760
accatgtgtg ctaattttt gtattttttta taaagatggg gatctcacta tgttgcccag    5820
gctggtcttg aactccagac ctcaagtgat cctcctgcct tggcctccca agctaaggg     5880 ggcattaaaa gaaaaaaaca ttttccccc tgaaacattt aagtagtctt actgaaaaca      5940
```

-continued

| | |
|---|---|
| ataaaacaca gaaacaccag attctcattt taaagtaaaa cagacaggat ctcccagaac | 6000 |
| cttcctagaa tggaaccatt cttgtcgctt ttgaaaaaca aagccaagtt ctagatccca | 6060 |
| aataaatgca cctgctggtg aacattctcc ttgtggttct cgtccctatg ttagttattt | 6120 |
| tcctaaattt tacatttgta ccttttaag aatgagttat cagttttttt atatttgctt | 6180 |
| ttcttttgag atggggtctt gctctgtcac ccaggctggg gtgcagtggt gcaatcacgg | 6240 |
| ctcactgcag cctcaacctc cagggctgaa gcgattctcc catctcagcc tcccatgttg | 6300 |
| agatcacagg tgtgcaccac cacacctggc tccttttcct gatttgtttt ttgtagagat | 6360 |
| gggatttcgc tatgttgccc aggctggtct ctaactcctg gactcaagtg atcctcccgc | 6420 |
| ctcagcttcc caaattgcta ggattacagg tttgagcccc tgcacctggt caacctgagt | 6480 |
| tttaagagga tcccttggc gactggattg aggacagaca agagtggacg ggggacacaa | 6540 |
| ggaggccatt ttcgttatcc aggcctggta gtggctaggg ccaggagggt ggggttggtg | 6600 |
| ggaagcagtc agatcccaaa gagatttggg gattggaagc aaaaggattt gctggtgact | 6660 |
| tgcacatggg agggagagag gtcagtgcct ctgttaatca aggaatccag attgccaccg | 6720 |
| aaatttctag gcccgagata tttaggtagt gtctcactct gtcacccagg atggagtgca | 6780 |
| gtggcgccat ctcggctcac tgtaacctcc gcctcccagg tttaaacgat tctcccacct | 6840 |
| cagcctcctg agtagctggg attacaggca tgtgccacca ctcccggcta attttgtat | 6900 |
| ttttagtaga cacggggttt caccacgttg gccaggctgg tcttgaactc ctgacctcaa | 6960 |
| gtgatccacc cacgacagcc tcccaaagtg ctgggattac aggcgtgagc caccatgctc | 7020 |
| ggccttttag gtggttttga gaggtattta ggtcacttcc aatctcgtgc ttttccaagt | 7080 |
| gttgtaaact acaaatattc cttcacgtct tcttgtcttt ttaatgttta gaaaaccta | 7140 |
| aaagaaatgt tccctattga ggcaggggcg atcaatccag agaacaggat catcccccac | 7200 |
| ctcccaggtg agcacgggc tgagccgcct gtcaggggt cattggcggg ggctcacctg | 7260 |
| ccctcccagc acctctcggg cttgacctca tgttctctgg tgccagctcc caagtggttt | 7320 |
| gacgggcagc gggccgccga gaaccaccag ggcacactta ccgagtactg cagcacgctc | 7380 |
| atgagcctgc ccaccaagat ctcccgctgt ccccacctcc ttgacttctt caaggtgcgc | 7440 |
| cctgatgacc tcaagctccc cacggacaac cagtgagtga acttttcacc ctgccaggtg | 7500 |
| ggagagggaa ggagggtgg gactttctgt gttttgcaga tgaggaaacc aaggctcaga | 7560 |
| gagggaaagc caccttccca gagccacaca gccagaaaga ggaggcaaat tccacctccg | 7620 |
| gcccctgtga ccccgccaag cctccacctt aatctttcac acctcagggc actggggaa | 7680 |
| gcactcgggg ctggaggttc aaagtcctgg gtcctcatcc tgacattatg ccacctggc | 7740 |
| catgggacct ggagccagtc accactgctc tctgaatgca ggttctccat ttctataatg | 7800 |
| ggcagtgagg atcagatgaa gcattgggtg tcttgcggag ccccccagaa ggatgtgggg | 7860 |
| ttgatgcctc tgctaagtgc tgagcatgtc tggggtctcc tgtacccagg accctgtgtg | 7920 |
| gaaggcacct gagaggctga gggagctcca ggcaggctgg ggaagtcccc ttctccactc | 7980 |
| ctctctggtc actgaagctc gaagtgggga gcatgaggac aggacgttac cccttgtcaa | 8040 |
| ggcacccagg ctgccaagac agagacaagc agcattgctc cggccagcac ttattgacgc | 8100 |
| ttgaaggtgt cccctggccc aaggaagggc agttatcatc agcccgggag gcggggaag | 8160 |
| gatggactct gcagtggggt ccgctcctca ttgcctgctc tctcagggct ccagaaggag | 8220 |
| gaagaggccg ggcacagtgg ctcacaccta taatcccagc actttggaag gtcgaggtgg | 8280 |
| gcagatcacc tgaggttggg agtttgagac cagcctggcc aacatggtga aaccccatct | 8340 |

```
ctaccaaaaa tataaaaatt tagtcaggca tggtggtgtg cgcttgtaat cccagctact   8400
tgggaggccg aggcaggaga atcgcttgaa cccgggaggc agaggttgca gtgagctgag   8460
actgcgccac tgcactccag cctgggtgac agagcgagac tctgtctaag aaaaaaaaaa   8520
gaaagaaga aagaagatgg cctgggagcc cgcaagagca ttttccaggc ttagggcatc    8580
ctttgggtct gcagaaggct atgcagtgtc tcctcatgt ccctcccttg ggctgcccga    8640
gcagatccgc ccgcccccat cacttcctga agcccttcct cagccagtcc agttgctgtc   8700
ttctctccgc agtgccccct ttccccttcccg gtccctctt ctcttgggaa gttcttctgc  8760
aggtctaccc agtgcctctt cttcctccat gggaagccaa gggtctcacc cagactgttc   8820
tctcctcagg acaaaaagc cagagacata cttgatgccc aaagatggca agagtaccgc    8880
gacaggtgag aggacggggg gcagccggcg gggggggaca ccctgaggag acccagagtg   8940
ttcagggaat ggagcagggg ctgggagcag gctgggaggg ctcacagcta ccctgctgaa   9000
gaattgggtc tttgggccgg gtgcggttgc tcatgcctgt aatcccagca gtttgggagg   9060
ccgaggcagg tggatcactt gaggtcagga gtttgagacc agcctggcca acatggagaa   9120
accctgtctc tactaaaaat ccaaattagc caggcgtggt gacaggtgcc tgtagtccca   9180
gccacttggg aggctgaggc aggagaattg cttgaacccg gaagacggag tttgcagtga   9240
gccgagatcg tgccactgca ctccagcctg gcagcagag ccagactcca tctcaaaaaa   9300
aaaaaaaaaa aagaagaatt gggtctttgg aaggtccctg gagactgaaa ggagcccttt  9360
gcaggtggca gtgcagagac cagcgcagac ccttgctact ggcagccggg ggagtgtttg   9420
cggctgaatg aatgaacagg ttttggaggg cagcgtggcc ttcagaggcg atgcagggct   9480
gtggcagttt ctaatactta ttgcacagtc actgctaata acaataataa taataatacc   9540
taacattaat ggagtgctta ctctgtgcca gccactattt tgttttttgt ttttcagtg    9600
acagggtctc gctctgttgc ccaggccaga gtgaagtggt gtgatcatag ctcactacag   9660
cctcgacctc ctgggctgaa gcgatcctcc cacctcagcc tcccaagtag ctgggattac   9720
aggtgtgtgc caccatgtcc agctaatttt taattttctg atagagatgg ggtctcacta   9780
cattgcccag gctggtctta agctcttggc ctcaagcaac cctcctgcct cagcctccca   9840
aagtgctgag attatagaca tgagccactg tgcccggctt tttcttcttc ttataaggac   9900
acgaggcctg ttgggttagg gcccactcta ctgacctcat tttaacttaa ttacctcttg   9960
aaacgtactc aagagtacct ttctcttaat acacccacac tgtaaggtac tgggtggtta  10020
ggacttcaac atatgaattt tgagaaggcg gatgtcagcc aataccaaac agcatcagca  10080
cctccacggt tggatgaagg gctggtcaga atgcacact caggtcccac agtggaccta   10140
ctgaacagga taggcatttt agcaaaatcc caggtattcg ggtgcacctt aaagttagga  10200
aaaggtcagg cactgtggct catgcctgta atcccagcac tttgggaggc cgaggcggtt  10260
gaatcacctg aggtcaggag ttcgagacca gcctgaccaa tatcgtgaaa ctccatctct  10320
actaaaaata caaaaattag ccaggtgtgg tggcgggtgc ttgtagtccc agctacttgg  10380
gaggctgagg caggtgaatt acttgaacct gggaggtgga ggttgcaatg agccaagatt  10440
gcaccactgc actccagtga cagagcgaga ctccatctca aaaaaaaaaa aaaaaaaagt  10500
tgggaaaagg ccaggtgcag tggctccacg cctgtaatcc caacactttta agaggctgag  10560
gtgggagaat cctttgagcc caggagttcg agaccagcct gggcattgtc caagaccctt  10620
gtctttacaa aaaattagcc gggtgtggtg gcatacgtct gtggtcccag ctattcggga  10680
ggctgaggca gggagattgc ttgagcctag gagtctaggg ctgtagtgag ctgtgatcac  10740
```

```
gtcactgtac tctagcctgg gcaacagagc aagactctgt ctccaaaaaa gaaaataaag    10800
ttgggaaagg ctcactaact tcatcagatg agaacaaaga catgtttgaa gtgtgaggcc    10860
gaagcctgga gaacgctatg cgcccaggaa atgcagggca gcagagactc aagatgccag    10920
cgcctgttct ggaggcccag atgggccctg caatgcccac tcaccctgcc ctccctcttg    10980
ccccagacat caccggcccc atcatcctgc agacgtaccg cgccattgcc gactacgaga    11040
agacctcggg ctccgagatg gctctgtcca cgggggacgt ggtggaggtc gtggagaaga    11100
gcgagagcgg tcagacctcc caccttacgg ggctccttcc cctggtgctc aggaacccac    11160
agccacaagc cccctgccaa ggctcaggca gcctggcccc tgggaggact ccagctctgt    11220 tagggggccct aaatgtcctc cccacactgt gggtcgcctt ctctcttagt gtgcaccctg    11280
tggtggctgt gggcatctgt gcatggcagg ccggggcggg gcatgtctgc gtgttctgtc    11340
tggatgggta tgggaccgtc tgttcattat gaagtgggct cagagctgtg attctgtgag    11400
catgtgtgca tgcatgcatg tgacctcatt gtccagtgtg gtgaaggtga catttccaaa    11460
tctgagcatt ggacatcagt gtgtctgtgt ccctgtgtcc tcaccatccc tgatggctgc    11520
agggagccgc tgggccctgc ccctcagtca cattcccgca cctctggcac aggttggtgg    11580
ttctgtcaga tgaaagcaaa gcgaggctgg atcccagcat ccttcctcga gcccctggac    11640
agtcctgacg agacggaaga ccctgagccc aactatgcag gtgcccctg ccctccgagg    11700 ctgtaggggt gtgggagaaa ggggcaggca gggctcaggg atattgagtg actgctttgg    11760
agtctgggct ggttgctggc ttggcagaaa agtcagggct aagatctcat cggctctggc    11820
ttgggggccc tggcaggttg tgatgcccctt ggtctggaca gggaaccagg aggaggagca    11880
gacgactcgg gagagtggga ggccagtggt gtctgtggat atgtgccag gttcagtggg    11940 aagctgaagg atgagcagac cttaggctca ggaaggaggg ctgcctggaa gtgggggcat    12000
catcactgac cagaaaggga aaactggcag tgccagggct ggatgggcc tgcattgagc    12060 ttgaaaaaaa ctataatagc attggttacc attttatttt attatttatt tatttatttt    12120 actttttttga gatagagtct cactcccttg ctaaggctgg agtgcggtgg tgctatctca    12180
gctcactgca acctctgcct cccaggatca agtgattctc cagcctcagc ctccccaggt    12240
agctgggatt acaagcatgc accaccatgc ctggataatt tttgtatttt tagttgagac    12300
ggggtttcac caggttggcc agactggtct cgaacttctg acctcaggtg atctgcctgc    12360
ctcggcctcc caaagtgctg gaattacaga tgtgagccac tgtccctggc ctggttaccc    12420
acattttaaa atggagtgat ttcaccctttt tatgtggatt tacagcttgt tttttttttt    12480
tttttgagac aaagtctggc tctgtcaccc aggctggagt gcagtaatgc aatctcagct    12540
cactgcaacc ttagcctcct gggttcaagc aattctcctg cctcagccac tgagtagcc    12600 tggggttaca ggcatgcacc accacgccag gctaattttt tgtatttta gtagagatgg    12660 ggtttcgcca tgttggccag gctggtctcg aactcctgac ctcaggtgat ccgcccgcct    12720
tggcctccca aagtgctagg attacaggtg gaaccacct gcccagcct gtggctatcg    12780 tttaaacact gggaaggcct gcagccccca ggccgacagt tagctgcagc tgagcagttc    12840
ccagtgccag gtagacggat gctccaccca cctactcatg gctgatctct tgtcatagtg    12900
aagtgtctgg acagaccttc atcgttatgg gatctctggt ccccagagtg ggtggcaatg    12960
aatgggagtg gacaagctca cctgggtgta ggggcagag gccgaagtc cagagtgtac    13020 ccccagagtg ggtgccagca ggagcttgcc gagggatctg gatggagca ggaggtgga    13080 gggaggagac ccagaagagg gggaactgtg ggccctgggt gggtctggag tgcctggagg    13140
```

-continued

```
aagcccaggc gcagagagga gaagatggga tgggtggcga gccccaggct gggccgacct    13200
cacactgtgc tctgtgcccc tgccgtggac caggtgagcc atacgtcgcc atcaaggcct    13260
acactgctgt ggaggggggac gaggtgtccc tgctcgaggg tgaagctgtt gaggtaattc    13320
acaagctcct ggacggctgg tgggtcatca ggtaggaggg cccctctcca tccagagcac    13380
ccatctgagt cagccccagc caggacgggg tgtttaggga tctggggtga cttgtccctg    13440
ggactctggg taagccactg cccctctctg gcttagttt ccatctcagt agcagggagg     13500
gatgagccca cccttgcctg tcttgtgggg atccaatgtc cttgtccaag tgggtgcatt    13560
tctcctttgt gatttagggt ctcttcccaa ccatctatta ttattccttc tctggcaaca    13620
tggtgaactg ttgtataaat aattacattc ctagctaggc gcaatggccc aggcctgtaa    13680
tcccagcact ttgggagccc aggacaggac gatcacgtga ggtcaggagt tcgagaccac    13740
cctggccaac atggcaaaac cctatctcta ctaaaaacac aaacatgagc cgggtgttgt    13800
ggtgggagcc tgtaatccca gctactcggg agtctgagac aagagaatca cttcaacccg    13860
ggaggcggag gttgcagtga gccaagatcg cgccattgca ctccagcctg gcaacgaga    13920 gcgaaactcc gtctcaaaaa aaaaaaaaa aaaaagatt actttctttt tatcattcct      13980
ttatctttta aagctttctt gcagtcaggt gcagtgtctc atgcctgtaa tcccaacact    14040
ttgggaagct gaggtgggag gatcactcaa ggctacaagt tcaagaccaa cctgggcaat    14100
gtagggagac ctctgtctct acaaaaaaaa ttaaaaaata gctggatgtg gtagcacaca    14160
cctgtagccc cagctactca ggaggctgag gtgaaaggat cacttgaccc caggagttgg    14220
aggcagcagt gagctatgac tgcaccactg caccccagcc tgggtgatgg agcaagaccc    14280
tgtctcaaaa aaaaaaaaa aaaaaagct tccattgcaa ttcccatctg tttatcctcc     14340
aaatgaatgc agaaatacta attatctttt ttctggttct ggggaacaca gaattctagc    14400
ggcttgtgga gccatttccc tggagccatg gggcctccca ggtcctttcc tgtgtcttca    14460 tttttttacga atttttttcat tttttgagac aggatcttgc tctgactccc aggctggagc   14520
acaatcatcg ctcactcaag cgatcctccc acctcaggct cccacgtagc tgggactaca    14580
ggtgagcacc accacatctg gctaatgttt tttaatttt ttgtagggt ggggtctcac      14640 tatggtgcca agactagtct taaactcctg gcctcaagag ttcctcctgc cttggcctcc    14700
caaagcactg ggattacagg aatgagcctc catgctgggc cttgctggc gtcttcagag     14760 ccctaggtca cagggccagc ctggcgcgcct gccgcaagct tatcttaaag ctgggaccac    14820
aacatgcata cctgcagccg ggcccggggc cagagggctt tgaggcagca tttctcagcc    14880
ttttagacac acactctgtt aacccccatc ctgtgtctct gataatcttc ttgtgatcct    14940
cccaccagcc aagaattggg ttttatgtga accttgtatt atgcaaagtt ttcttttgtt    15000
ttttttttca ctcccaaata taatattgag aatagaaaga aagtcttttc aacaaatggt    15060
gctggaacag atggatttcc atactggaaa aaaaaaaaa agagcaaaaa acaaacctag     15120
accccttcct cacactgtac acatatgttt acttcagatg gatcacaggt ttatcccaga    15180
gtaaaacctg aaactaaaaa ccatttgggg ctggacaggg agctcacgcc tgtaatctca    15240
gcactttggg aggctgaggc aggtggatca cttgatgtca ggagtttgag accagccatg    15300
accaatatgg tgaaatcctg tctctactaa aaaatacaa aattaaccaa gtgtggtggt     15360
gcatgcctgt aatcccagct acttgggaag ctgagacagg agaattgctt gaacttggga    15420
agcagaggtt gcaatgagtc gacatcatgc cattgcactc cagcctaggc aacaagagca    15480
aaactctgtc ttggggttgg gtggggaaa agcatttgga agaaagcata gaatttggtg    15540
```

-continued

```
gcttggaggt aggcaaaggt tcgtaggaga cagaaggcag ttaacataaa agaaaaattg    15600
gcaaatataa tcctgccagt gtcttctttt ttctttaatt ttttcgggag gtagagatag    15660
gggtcttgct atgttaccca ggctgatctc caactcctgg cctcaagcga tcctcccacc    15720
tagatccctc aaagtactgg gattacaggc gtgagcgacc gtgccctgcc cattcttgcc    15780
aatgtcttat agcaaatacc tgtccctgc ggtgacctgg atctgctaac ctccaccct     15840 gcctagactg tggaaggatt gctggaaggg tctcagttgc acagaccagg aaactgaggc    15900
ccacagaggc aggtgtccgg ttgtttgcaa cctctcagcc tgtgctaacc ccaattgttc    15960
agagagagcc ctgaaaccct ctcctctggg cgcccccagg tgactgcccc agcctcaagg    16020
gctgcctctg ttgcaggaaa gacgacgtca caggctactt cccgtccatg tacctgcaaa    16080
agtcagggca agacgtgtcc caggcccaac gccagatcaa gcgggggggcg ccgccccgca    16140 ggtaagcggg gtccccgggg ctgggcggg gtcgagcggg gcgcaccacg ggttcgctct    16200
gtctaggcca tagcttggca gtgccggggc gggggctctc agcctggcag gagaggcagg    16260
accctcacgg gggaaagggg ctggacgcgc ctggccgcgg tgtggggctg gcacgggggc    16320
ggaaggaaag cggcgatgcc cgggggcttt gggatgggc agtccagggg ggctccccgg    16380 agaggggac gacagaccga aggctggtga ggggcgtgga aaaccgccca ggctctgctg    16440
cagggcaagg gtccttgtcg tgacggggggc agccgcctct tgtcccgccg gggtcgtgca    16500
gactaccggc cccctactgc cccccacttc ctcggaccag gggtgcccat ctgagtccct    16560 ggggggcaggg gcgccctcgg gctttgacga cgccccgtcc cgctgggcca ggtcgtccat    16620
ccgcaacgcg cacagcatcc accagcggtc gcggaagcgc ctcagccagg acgcctatcg    16680
ccgcaacagc gtccgttttc tgcagcagcg acgccgccag gcgcggccgg gaccgcagag    16740
ccccgggagc ccgctcggtg agtgcagcgg gagagggcag gaagggcaag ccctagggc    16800 ggagtcagcg ggagaggcgg ggccagaggc agggccagag tagcgggggcg ggaccagagg    16860 gcggaatcag agggagaggc ggggactgga ggcggggggca gaggaggagc cagcgctagg    16920
gggcggagcg atccctaaga ggcggagtca gaggggagagg cacaagcggg aggcgaggcc    16980
agagcgcgga gcaggagttg gagaccgcgg cgggggcgagg ccagagagcg ctgtgggcgg    17040
ggccagtgtg cggggcgggg cgtctgactc ggccccgctc tctgcccgca gaggaggagc    17100
ggcagacgca gcgctctaaa ccgcagccgg cggtgccccc gcggccgagc gccgacctca    17160
tcctgaaccg ctgcagcgag agcaccaagc ggaagctggc gtctgccgtc tgaggctgga    17220
gcgcagtccc cagctagcgt ctcggccctt gccgccccgt gcctgtatat acgtgttcta    17280
tagagcctgg cgtctggacg ccgagggcag ccccgacccc tgtccagcgc ggctcccgcc    17340
accctcaata aatgttgctt ggagtggacc gaggctctgc aggaatgcag ggagggccgg    17400
gctccgcccc agggttattt tctaagttga ggacagggag gttgtgagtt ctgnnnnnnn    17460
nnnnnnnnnn nnnnnnnnnn nnnnnnnnnn nnnnnnnnnn nnnnnnnnnn nnnnnnnnnn    17520
nnnnnnnnnn nnnnnnnnnn nnnnnnnnnn nnnnnnnnnn nnnnnnnnnn nnnnnnnnnn    17580
nnnnnnnnnn nnnnnnnnnn nnnnnnnnnn nnnnnnnnnn nnnnnnnnnn nnnnnnnnnn    17640
nnnnnnnnnn nnnnnnnnnn nnnnnnnnnn nnnnnnnnnn nnnnnnnnnn nnnnnnnnnn    17700
nnnnnnnnnn nnnnnnnnnn nnnnnnnnnn nnnnnnnnnn nnnnnnnnnn nnnnnnnnnn    17760
nnnnnnnnnn nnnnnnnnnn nnnnnnnnnn nnnnnnnnnn nnnnnnnnnn nnnnnnnnnn    17820
nnnnnnnnnn nnnnnnnnnn nnnnnnnnnn nnnnnnnnnn nnnnnnnnnn nnnnnnnnnn    17880
nnnnnnnnnn nnnnnnnnnn nnnnnnnnnn nnnnnnnnnn nnnnnnnnnn nnnnnnnnnn    17940
```

-continued

```
nnnnnnnnnn nnnnnnnnnn nnnnnnnnnn nnnnnnnnnn nnnnnnnnnn nnnnnnnnnn    18000
nnnnnnnnnn nnnnnnnnnn nnnnnnnnnn nnnnnnnnnn nnnnnnnnnn nnnnnnnnnn    18060
nnnnnntaaa aattagctgg gcgtggtggc atgcatccac aatcccagct actgggagg      18120 ctgaggcatg agaatcgctt gaaccgggga ggcagatgtt gcagtgagcc gagacggcgc    18180
cactgcactc cagcctggac tacagagcga gactctatct caaaaaaaaa aaaaaaaaa     18240 aagtaactta ggtgcagggt gtcctctgtt attcactgag accgtgcccc ggttatgagg    18300
ttgtaccaga aagcaagtat tcactatgca cactattcac cgctcaccct agcattgaaa    18360
ccagcctgta gcctgaaagc ctttgctttg agggcaggtc tttccccaaa atgcagacac    18420
gaaggtgcaa agtgaagctg ccagtcttgc aaaagatgta acttgtcacg aaggccacga    18480
gtggcaggga gagctgtccc acatttgcgg aagtggctat gtgaggacgg gggaggcggg    18540
tcccttagag ataagagaca atcataaggg gagatatcag agaaaatcgt aaggggagca    18600
gatggttgtc aagagaatag gctgaccatc gaaggactgg cagaagcttt cagaaaacca    18660
ctggacggct gggcacagtg gcttaggcct gtaatcccag cactttggga ggctgacgca    18720
ggtgaatcac ttgaggtcag gagttccaga ccagcctggc caacatggtg aaaccccatc    18780
tctacagaaa atataaaaat tagccaggcg tggtggcaca agcctagaat cccagctact    18840
tgggaggctg agg                                                        18853
```

<210> SEQ ID NO 4
<211> LENGTH: 390
<212> TYPE: PRT
<213> ORGANISM: Homo sapien

<400> SEQUENCE: 4

```
Met Gly Asp Thr Phe Ile Arg His Ile Ala Leu Leu Gly Phe Glu Lys
  1               5                  10                  15

Arg Phe Val Pro Ser Gln His Tyr Val Tyr Met Phe Leu Val Lys Trp
             20                  25                  30

Gln Asp Leu Ser Glu Lys Val Val Tyr Arg Arg Phe Thr Glu Ile Tyr
         35                  40                  45

Glu Phe His Lys Thr Leu Lys Glu Met Phe Pro Ile Glu Ala Gly Ala
     50                  55                  60

Ile Asn Pro Glu Asn Arg Ile Ile Pro His Leu Pro Ala Pro Lys Trp
 65                  70                  75                  80

Phe Asp Gly Gln Arg Ala Ala Glu Asn Arg Gln Gly Thr Leu Thr Glu
                 85                  90                  95

Tyr Cys Ser Thr Leu Met Ser Leu Pro Thr Lys Ile Ser Arg Cys Pro
            100                 105                 110

His Leu Leu Asp Phe Phe Lys Val Arg Pro Asp Asp Leu Lys Leu Pro
        115                 120                 125

Thr Asp Asn Gln Thr Lys Lys Pro Glu Thr Tyr Leu Met Pro Lys Asp
    130                 135                 140

Gly Lys Ser Thr Ala Thr Asp Ile Thr Gly Pro Ile Ile Leu Gln Thr
145                 150                 155                 160

Tyr Arg Ala Ile Ala Asp Tyr Glu Lys Thr Ser Gly Ser Glu Met Ala
                165                 170                 175

Leu Ser Thr Gly Asp Val Val Glu Val Val Glu Lys Ser Glu Ser Gly
            180                 185                 190

Trp Trp Phe Cys Gln Met Lys Ala Lys Arg Gly Trp Ile Pro Ala Ser
        195                 200                 205
```

```
                                    -continued

Phe Leu Glu Pro Leu Asp Ser Pro Asp Glu Thr Glu Asp Pro Glu Pro
    210                 215                 220

Asn Tyr Ala Gly Glu Pro Tyr Val Ala Ile Lys Ala Tyr Thr Ala Val
225                 230                 235                 240

Glu Gly Asp Glu Val Ser Leu Leu Glu Gly Glu Ala Val Glu Val Ile
                245                 250                 255

His Lys Leu Leu Asp Gly Trp Trp Val Ile Arg Lys Asp Asp Val Thr
            260                 265                 270

Gly Tyr Phe Pro Ser Met Tyr Leu Gln Lys Ser Gly Gln Asp Val Ser
        275                 280                 285

Gln Ala Gln Arg Gln Ile Lys Arg Gly Ala Pro Pro Arg Arg Ser Ser
    290                 295                 300

Ile Arg Asn Ala His Ser Ile His Gln Arg Ser Arg Lys Arg Leu Ser
305                 310                 315                 320

Gln Asp Ala Tyr Arg Arg Asn Ser Val Arg Phe Leu Gln Gln Arg Arg
                325                 330                 335

Arg Gln Ala Arg Pro Gly Pro Gln Ser Pro Gly Ser Pro Leu Glu Glu
            340                 345                 350

Glu Arg Gln Thr Gln Arg Ser Lys Pro Gln Pro Ala Val Pro Pro Arg
        355                 360                 365

Pro Ser Ala Asp Leu Ile Leu Asn Arg Cys Ser Glu Ser Thr Lys Arg
    370                 375                 380

Lys Leu Ala Ser Ala Val
385                 390
```

ISOLATED HUMAN ENZYME PROTEINS, NUCLEIC ACID MOLECULES ENCODING HUMAN ENZYME PROTEINS, AND USES THEREOF

This application claims priority to U.S. application Ser. No. 09/820,005 filed Mar. 29, 2001, now U.S. Pat. No. 6,489,149.

FIELD OF THE INVENTION

The present invention is in the field of enzyme proteins that are related to the NADPH oxidase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Many human enzymes serve as targets for the action of pharmaceutically active compounds. Several classes of human enzymes that serve as such targets include helicase, steroid esterase and sulfatase, convertase, synthase, dehydrogenase, monoxygenase, transferase, kinase, glutanase, decarboxylase, isomerase and reductase. It is therefore important in developing new pharmaceutical compounds to identify target enzyme proteins that can be put into high-throughput screening formats. The present invention advances the state of the art by providing novel human drug target enzymes related to the NADPH oxidase subfamily.

Neutrophil NADPH oxidase is a multicomponent enzyme that is activated to generate superoxide anion and is defective in the cells of patients with chronic granulomatous disease. It requires both membrane and cytosolic components, the latter including 47- and 67-kDa proteins recognized by the polyclonal antiserum B-1. Immunoscreening of an induced HL-60 lambda ZAP cDNA library yielded seven cross-hybridizing cDNAs encoding the 47-kDa component. Fusion proteins of 22–50 kDa were recognized by B-1. Antiserum against a fusion protein recognized a 47-kDa protein in normal neutrophils but not in those from patients with autosomal chronic granulomatous disease who lack the 47-kDa cytosolic oxidase component.

The phagocyte NADPH oxidase is a complex enzyme system that plays an important role in host defense. After stimulation with opsonized microorganisms or other activating agents, the oxygen consumption of these cells increases dramatically (respiratory burst) and they release a large amount of superoxide. Superoxide is then converted to more potent reactive oxygen species such as hydrogen peroxide, hydroxyl radical, and hypohalous acids, which are used by phagocytes to control microbial infections. The importance of this defense mechanism is made evident by a rare inherited syndrome, chronic granulomatous disease (CGD) in which phagocytes fail to generate superoxide, rendering the patients highly susceptible to life-threatening microbial infections.

The present invention has a substantial similarity to p47phox. The cDNA of this enzyme was originally isolated for the 47-kilodalton (kDa) subunit of the NADPH oxidase system, whose absence is responsible for the most common form of autosomally inherited chronic granulomatous disease (CGD). It encodes a 44.7-kDa polypeptide, which contains two src homology (SH3) domains and several possible sites for phosphorylation by protein kinase C. An antiserum raised to the predicted C terminus of the protein detects a polypeptide with an apparent molecular mass of 47 kDa in normal neutrophil granulocytes but not in those from patients with autosomal CGD. The antibody has been used to show that the protein associates with the vacuolar membrane and is phosphorylated in response to phorbol ester treatment. Analysis of a number of tissue types and cell lines shows that expression of the gene is confined to phagocytic cells and B lymphocytes. It is suggested that patients with CGD may also have a defect in lymphocyte function. p47 protein and mRNA levels increase during retinoic acid-induced neutrophil differentiation of HL60 cells. The gene is a primary target for regulation by retinoic acid. For a review related to p47 phox, see Rodaway et al., Mol Cell Biol October 1990; 10(10):5388–96; Volpp et al., Proc Natl Acad Sci U S A September 1989; 86(18):7195–9 Erratum in: Proc Natl Acad Sci U S A December 1989; 86(23):9563.

Enzyme proteins, particularly members of the NADPH oxidase subfamily, are a major target for drug action and development. Accordingly, it is valuable to the field of pharmaceutical development to identify and characterize previously unknown members of this subfamily of enzyme proteins. The present invention advances the state of the art by providing previously unidentified human enzyme proteins, and the polynucleotides encoding them, that have homology to members of the NADPH oxidase subfamily. These novel compositions are useful in the diagnosis, prevention and treatment of biological processes associated with human diseases.

SUMMARY OF THE INVENTION

The present invention is based in part on the identification of amino acid sequences of human enzyme peptides and proteins that are related to the NADPH oxidase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate enzyme activity in cells and tissues that express the enzyme. Experimental data as provided in FIG. 1 indicates expression in humans in the placenta, B cells from Burkitt lymphoma, primary B-cells from tonsils and leukocyte.

DESCRIPTION OF THE FIGURE SHEETS

FIG. 1 provides the nucleotide sequence of a cDNA molecule or transcript sequence that encodes the enzyme protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in the placenta, B cells from Burkitt lymphoma, primary B-cells from tonsils and leukocyte.

FIGS. 2A–2C provide the predicted amino acid sequence of the enzyme of the present invention. (SEQ ID NO:2) In addition structure and functional information such as protein family, function, and modification sites is provided where available, allowing one to readily determine specific uses of inventions based on this molecular sequence.

FIGS. 3A–3O provide genomic sequences that span the gene encoding the enzyme protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs, including insertion/deletion variants ("indels"), were identified at 41 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a enzyme protein or part of a enzyme protein and are related to the NADPH oxidase subfamily. Utilizing these sequences, additional genomic sequences were assembled and transcript and/or cDNA sequences were isolated and characterized. Based on this analysis, the present invention provides amino acid sequences of human enzyme peptides and proteins that are related to the NADPH oxidase subfamily, nucleic acid sequences in the form of transcript sequences, cDNA sequences and/or genomic sequences that encode these enzyme peptides and proteins, nucleic acid variation (allelic information), tissue distribution of expression, and information about the closest art known protein/peptide/domain that has structural or sequence homology to the enzyme of the present invention.

In addition to being previously unknown, the peptides that are provided in the present invention are selected based on their ability to be used for the development of commercially important products and services. Specifically, the present peptides are selected based on homology and/or structural relatedness to known enzyme proteins of the NADPH oxidase subfamily and the expression pattern observed. Experimental data as provided in FIG. 1 indicates expression in humans in the placenta, B cells from Burkitt lymphoma, primary B-cells from tonsils and leukocyte. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known NADPH oxidase family or subfamily of enzyme proteins.

Specific Embodiments

Peptide Molecules

The present invention provides nucleic acid sequences that encode protein molecules that have been identified as being members of the enzyme family of proteins and are related to the NADPH oxidase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the enzyme peptides of the present invention, enzyme peptides, or peptides/proteins of the present invention.

The present invention provides isolated peptide and protein molecules that consist of, consist essentially of, or comprise the amino acid sequences of the enzyme peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the enzyme peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated enzyme peptide can be purified from cells that naturally express it, purified from cells that have been altered to express it (recombinant), or synthesized using known protein synthesis methods. Experimental data as provided in FIG. 1 indicates expression in humans in the placenta, B cells from Burkitt lymphoma, primary B-cells from tonsils and leukocyte. For example, a nucleic acid molecule encoding the enzyme peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the enzyme peptides of the present invention are the naturally occurring mature proteins. A brief description of how various types of these proteins can be made/isolated is provided below.

The enzyme peptides of the present invention can be attached to heterologous sequences to form chimeric or fusion proteins. Such chimeric and fusion proteins comprise a enzyme peptide operatively linked to a heterologous protein having an amino acid sequence not substantially homologous to the enzyme peptide. "Operatively linked" indicates that the enzyme peptide and the heterologous protein are fused in-frame. The heterologous protein can be fused to the N-terminus or C-terminus of the enzyme peptide.

In some uses, the fusion protein does not affect the activity of the enzyme peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant enzyme peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A enzyme peptide-encoding nucleic acid can be cloned into such an expression vector such that the fusion moiety is linked in-frame to the enzyme peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the enzyme peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWS-gapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the enzyme peptides of the present invention as well as being encoded by the same genetic locus as the enzyme peptide provided herein. As indicated by the data presented in FIG. 3, the map position was determined to be on chromosome 19 by ePCR.

Allelic variants of a enzyme peptide can readily be identified as being a human protein having a high degree (significant) of sequence homology/identity to at least a portion of the enzyme peptide as well as being encoded by the same genetic locus as the enzyme peptide provided herein. Genetic locus can readily be determined based on the genomic information provided in FIG. 3, such as the genomic sequence mapped to the reference human. As indicated by the data presented in FIG. 3, the map position was determined to be on chromosome 19 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a enzyme peptide encoding nucleic acid molecule under stringent conditions as more fully described below.

FIG. 3 provides information on SNPs that have been identified in a gene encoding the enzyme protein of the present invention. 41 SNP variants were found, including 7 indels (indicated by a "-") and 4 SNPs in exons, of which 2 of these cause changes in the amino acid sequence (i.e., nonsynonymous SNPs). The changes in the amino acid sequence that these SNPs cause is indicated in FIG. 3 and can readily be determined using the universal genetic code and the protein sequence provided in FIG. 2 as a reference. SNPs, identified at different nucleotide positions in introns and regions 5' and 3' of the ORF, may affect control/regulatory elements.

Paralogs of a enzyme peptide can readily be identified as having some degree of significant sequence homology/identity to at least a portion of the enzyme peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a enzyme peptide encoding nucleic acid molecule under moderate to stringent conditions as more fully described below.

Orthologs of a enzyme peptide can readily be identified as having some degree of significant sequence homology/identity to at least a portion of the enzyme peptide as well as being encoded by a gene from another organism. Preferred orthologs will be isolated from mammals, preferably primates, for the development of human therapeutic targets and agents. Such orthologs will be encoded by a nucleic acid sequence that will hybridize to a enzyme peptide encoding nucleic acid molecule under moderate to stringent conditions, as more fully described below, depending on the degree of relatedness of the two organisms yielding the proteins.

Non-naturally occurring variants of the enzyme peptides of the present invention can readily be generated using recombinant techniques. Such variants include, but are not limited to deletions, additions and substitutions in the amino acid sequence of the enzyme peptide. For example, one class of substitutions are conserved amino acid substitution. Such substitutions are those that substitute a given amino acid in a enzyme peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant enzyme peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as enzyme activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the enzyme peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a enzyme peptide. Such fragments can be chosen based on the ability to retain one or more of the biological activities of the enzyme peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the enzyme peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in enzyme peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the enzyme peptides of the present invention also encompass derivatives or analogs in which a substituted amino acid residue is not one encoded by the genetic code, in which a substituent group is included, in which the mature enzyme peptide is fused with another compound, such as a compound to increase the half-life of the enzyme peptide (for example, polyethylene glycol), or in which the additional amino acids are fused to the mature enzyme peptide, such as a leader or secretory sequence or a sequence for purification of the mature enzyme peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a enzyme-effector protein interaction or enzyme-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, enzymes isolated from humans and their human/mammalian orthologs serve as targets for identifying agents for use in mammalian therapeutic applications, e.g. a human drug, particularly in modulating a biological or pathological response in a cell or tissue that expresses the enzyme. Experimental data as provided in FIG. 1 indicates that the enzymes of the present invention are expressed in humans in the placenta, B cells from Burkitt lymphoma, primary B-cells from tonsils detected by a virtual northern blot. In addition, PCR-based tissue screening panels indicate expression in and leukocyte. A large percentage of pharmaceutical agents are being developed that modulate the activity of enzyme proteins, particularly members of the NADPH oxidase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the placenta, B cells from Burkitt lymphoma, primary B-cells from tonsils and leukocyte. Such uses can readily be determined using the information provided herein, that which is known in the art, and routine experimentation.

The proteins of the present invention (including variants and fragments that may have been disclosed prior to the present invention) are useful for biological assays related to enzymes that are related to members of the NADPH oxidase subfamily. Such assays involve any of the known enzyme functions or activities or properties useful for diagnosis and treatment of enzyme-related conditions that are specific for the subfamily of enzymes that the one of the present invention belongs to, particularly in cells and tissues that express the enzyme. Experimental data as provided in FIG. 1 indicates that the enzymes of the present invention are expressed in humans in the placenta, B cells from Burkitt lymphoma, primary B-cells from tonsils detected by a virtual northern blot. In addition, PCR-based tissue screening panels indicate expression in and leukocyte.

The proteins of the present invention are also useful in drug screening assays, in cell-based or cell-free systems. Cell-based systems can be native, i.e., cells that normally express the enzyme, as a biopsy or expanded in cell culture. Experimental data as provided in FIG. 1 indicates expression in humans in the placenta, B cells from Burkitt lymphoma, primary B-cells from tonsils and leukocyte. In an alternate embodiment, cell-based assays involve recombinant host cells expressing the enzyme protein.

The polypeptides can be used to identify compounds that modulate enzyme activity of the protein in its natural state or an altered form that causes a specific disease or pathology associated with the enzyme. Both the enzymes of the present invention and appropriate variants and fragments can be used in high-throughput screens to assay candidate compounds for the ability to bind to the enzyme. These compounds can be further screened against a functional enzyme to determine the effect of the compound on the enzyme activity. Further, these compounds can be tested in animal or invertebrate systems to determine activity/effectiveness. Compounds can be identified that activate (agonist) or inactivate (antagonist) the enzyme to a desired degree.

Further, the proteins of the present invention can be used to screen a compound for the ability to stimulate or inhibit interaction between the enzyme protein and a molecule that normally interacts with the enzyme protein, e.g. a substrate or a component of the signal pathway that the enzyme protein normally interacts (for example, another enzyme). Such assays typically include the steps of combining the enzyme protein with a candidate compound under conditions that allow the enzyme protein, or fragment, to interact with the target molecule, and to detect the formation of a complex between the protein and the target or to detect the biochemical consequence of the interaction with the enzyme protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant enzymes or appropriate fragments containing mutations that affect enzyme function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) enzyme activity. The assays typically involve an assay of events in the signal transduction pathway that indicate enzyme activity. Thus, the phosphorylation of a substrate, activation of a protein, a change in the expression of genes that are up- or down-regulated in response to the enzyme protein dependent signal cascade can be assayed.

Any of the biological or biochemical functions mediated by the enzyme can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the enzyme can be assayed. Experimental data as provided in FIG. 1 indicates that the enzymes of the present invention are expressed in humans in the placenta, B cells from Burkitt lymphoma, primary B-cells from tonsils detected by a virtual northern blot. In addition, PCR-based tissue screening panels indicate expression in and leukocyte.

Binding and/or activating compounds can also be screened by using chimeric enzyme proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native enzyme. Accordingly, a different set of signal transduction components is available as an end-point assay for activation. This allows for assays to be performed in other than the specific host cell from which the enzyme is derived.

The proteins of the present invention are also useful in competition binding assays in methods designed to discover compounds that interact with the enzyme (e.g. binding partners and/or ligands). Thus, a compound is exposed to a enzyme polypeptide under conditions that allow the compound to bind or to otherwise interact with the polypeptide. Soluble enzyme polypeptide is also added to the mixture. If the test compound interacts with the soluble enzyme polypeptide, it decreases the amount of complex formed or activity from the enzyme target. This type of assay is particularly useful in cases in which compounds are sought that interact with specific regions of the enzyme. Thus, the soluble polypeptide that competes with the target enzyme region is designed to contain peptide sequences corresponding to the region of interest.

To perform cell free drug screening assays, it is sometimes desirable to immobilize either the enzyme protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of enzyme-binding protein found in the bead fraction quantitated from the gel using standard electrophoretic techniques.

For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a enzyme-binding protein and a candidate compound are incubated in the enzyme protein-presenting wells and the amount of complex trapped in the well can be quantitated. Methods for detecting such complexes, in addition to those described above for the GST-immobilized complexes, include immunodetection of complexes using antibodies reactive with the enzyme protein target molecule, or which are reactive with enzyme protein and compete with the target molecule, as well as enzyme-linked assays which rely on detecting an enzymatic activity associated with the target molecule.

Agents that modulate one of the enzymes of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of enzyme protein activity identified according to these drug screening assays can be used to treat a subject with a disorder mediated by the enzyme pathway, by treating cells or tissues that express the enzyme. Experimental data as provided in FIG. 1 indicates expression in humans in the placenta, B cells from Burkitt lymphoma, primary B-cells from tonsils and leukocyte. These methods of treatment include the steps of administering a modulator of enzyme activity in a pharmaceutical composition to a subject in need of such treatment, the modulator being identified as described herein.

In yet another aspect of the invention, the enzyme proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the enzyme and are involved in enzyme activity. Such enzyme-binding proteins are also likely to be involved in the propagation of signals by the enzyme proteins or enzyme targets as, for example, downstream elements of a enzyme-mediated signaling pathway. Alternatively, such enzyme-binding proteins are likely to be enzyme inhibitors.

The two-hybrid system is based on the modular nature of most transcription factors, which consist of separable DNA-binding and activation domains. Briefly, the assay utilizes two different DNA constructs. In one construct, the gene that codes for a enzyme protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a enzyme-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the enzyme protein.

This invention further pertains to novel agents identified by the above-described screening assays. Accordingly, it is within the scope of this invention to further use an agent identified as described herein in an appropriate animal model. For example, an agent identified as described herein (e.g., a enzyme-modulating agent, an antisense enzyme nucleic acid molecule, a enzyme-specific antibody, or a enzyme-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The enzyme proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the placenta, B cells from Burkitt lymphoma, primary B-cells from tonsils and leukocyte. The method involves contacting a biological sample with a compound capable of interacting with the enzyme protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered enzyme activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the enzyme protein in which one or more of the enzyme functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and enzyme activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the placenta, B cells from Burkitt lymphoma, primary B-cells from tonsils and leukocyte. Accordingly, methods for treatment include the use of the enzyme protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the enzyme proteins. Antibodies can be prepared from any region of the peptide as described herein. However, preferred regions will include those involved in function/activity and/or enzyme/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylanine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the enzymes of the present invention are expressed in humans in the placenta, B cells from Burkitt lymphoma, primary B-cells from tonsils detected by a virtual northern blot. In addition, PCR-based tissue screening panels indicate expression in and leukocyte. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the placenta, B cells from Burkitt lymphoma, primary B-cells from tonsils and leukocyte. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the placenta, B cells from Burkitt lymphoma, primary B-cells from tonsils and leukocyte. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the placenta, B cells from Burkitt lymphoma, primary B-cells from tonsils and leukocyte. Thus, where a specific protein has been correlated with expression in a specific tissue, antibodies that are specific for this protein can be used to identify a tissue type.

The antibodies are also useful for inhibiting protein function, for example, blocking the binding of the enzyme peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a enzyme peptide or protein of the present invention (cDNA, transcript and genomic sequence). Such nucleic acid molecules will consist of, consist essentially of, or comprise a nucleotide sequence that encodes one of the enzyme peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the enzyme peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the enzyme proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 19 by ePCR.

FIG. 3 provides information on SNPs that have been identified in a gene encoding the enzyme protein of the present invention. 41 SNP variants were found, including 7 indels (indicated by a "-") and 4 SNPs in exons, of which 2 of these cause changes in the amino acid sequence (i.e., nonsynonymous SNPs). The changes in the amino acid sequence that these SNPs cause is indicated in FIG. 3 and can readily be determined using the universal genetic code and the protein sequence provided in FIG. 2 as a reference SNPs, identified at different nucleotide positions in introns and regions 5' and 3' of the ORF, may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, New York (1989), 6.3.1–6.3.6. One example of stringent hybridization conditions are hybridization in 6× sodium chloride/sodium citrate (SSC) at about 45

C., followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs, including insertion/deletion variants ("indels"), were identified at 41 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 19 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the enzymes of the present invention are expressed in humans in the placenta, B cells from Burkitt lymphoma, primary B-cells from tonsils detected by a virtual northern blot. In addition, PCR-based tissue screening panels indicate expression in and leukocyte. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in enzyme protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a enzyme protein, such as by measuring a level of a enzyme-encoding nucleic acid in a sample of cells from a subject e.g., mRNA or genomic DNA, or determining if a enzyme gene has been mutated. Experimental data as provided in FIG. 1 indicates that the enzymes of the present invention are expressed in humans in the placenta, B cells from Burkitt lymphoma, primary B-cells from tonsils detected by a virtual northern blot. In addition, PCR-based tissue screening panels indicate expression in and leukocyte.

Nucleic acid expression assays are useful for drug screening to identify compounds that modulate enzyme nucleic acid expression.

The invention thus provides a method for identifying a compound that can be used to treat a disorder associated with nucleic acid expression of the enzyme gene, particularly biological and pathological processes that are mediated by the enzyme in cells and tissues that express it. Experimental data as provided in FIG. 1 indicates expression in humans in the placenta, B cells from Burkitt lymphoma, primary B-cells from tonsils and leukocyte. The method typically includes assaying the ability of the compound to modulate the expression of the enzyme nucleic acid and thus identifying a compound that can be used to treat a disorder characterized by undesired enzyme nucleic acid expression. The assays can be performed in cell-based and cell-free systems. Cell-based assays include cells naturally expressing the enzyme nucleic acid or recombinant cells genetically engineered to express specific nucleic acid sequences.

The assay for enzyme nucleic acid expression can involve direct assay of nucleic acid levels, such as mRNA levels, or on collateral compounds involved in the signal pathway. Further, the expression of genes that are up- or down-regulated in response to the enzyme protein signal pathway can also be assayed. In this embodiment the regulatory regions of these genes can be operably linked to a reporter gene such as luciferase.

Thus, modulators of enzyme gene expression can be identified in a method wherein a cell is contacted with a candidate compound and the expression of mRNA determined. The level of expression of enzyme mRNA in the presence of the candidate compound is compared to the level of expression of enzyme mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate enzyme nucleic acid expression in cells and tissues that express the enzyme. Experimental data as provided in FIG. 1 indicates that the enzymes of the present invention are expressed in humans in the placenta, B cells from Burkitt lymphoma, primary B-cells from tonsils detected by a virtual northern blot. In addition, PCR-based tissue screening panels indicate expression in and leukocyte. Modulation includes both up-regulation (i.e. activation or agonization) or down-regulation (suppression or antagonization) or nucleic acid expression.

Alternatively, a modulator for enzyme nucleic acid expression can be a small molecule or drug identified using the screening assays described herein as long as the drug or small molecule inhibits the enzyme nucleic acid expression in the cells and tissues that express the protein. Experimental data as provided in FIG. 1 indicates expression in humans in the placenta, B cells from Burkitt lymphoma, primary B-cells from tonsils and leukocyte.

The nucleic acid molecules are also useful for monitoring the effectiveness of modulating compounds on the expression or activity of the enzyme gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in enzyme nucleic acid expression, and particularly in qualitative changes that lead to pathology. The nucleic acid molecules can be used to detect mutations in enzyme genes and gene expression products such as mRNA. The nucleic acid molecules can be used as hybridization probes to detect naturally occurring genetic mutations in the enzyme gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the enzyme gene associated with a dysfunction provides a diagnostic tool for an active disease or susceptibility to disease when the disease results from overexpression, underexpression, or altered expression of a enzyme protein.

Individuals carrying mutations in the enzyme gene can be detected at the nucleic acid level by a variety of techniques. FIG. 3 provides information on SNPs that have been identified in a gene encoding the enzyme protein of the present invention. 41 SNP variants were found, including 7 indels (indicated by a "-") and 4 SNPs in exons, of which 2 of these cause changes in the amino acid sequence (i.e., nonsynonymous SNPs). The changes in the amino acid sequence that these SNPs cause is indicated in FIG. 3 and can readily be determined using the universal genetic code and the protein sequence provided in FIG. 2 as a reference SNPs, identified at different nucleotide positions in introns and regions 5' and 3' of the ORF, may affect control/regulatory elements. As indicated by the data presented in FIG. 3, the map position was determined to be on chromosome 19 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a enzyme gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant enzyme gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the enzyme gene in an individual in order to select an appropriate compound or dosage regimen for treatment. FIG. 3 provides information on SNPs that have been identified in a gene encoding the enzyme protein of the present invention. 41 SNP variants were found, including 7 indels (indicated by a "-") and 4 SNPs in exons, of which 2 of these cause changes in the amino acid sequence (i.e., nonsynonymous SNPs). The changes in the amino acid sequence that these SNPs cause is indicated in FIG. 3 and can readily be determined using the universal genetic code and the protein sequence provided in FIG. 2 as a reference SNPs, identified at different nucleotide positions in introns and regions 5' and 3' of the ORF, may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control enzyme gene expression in cells, tissues, and organisms. A DNA antisense nucleic acid molecule is designed to be complementary to a region of the gene involved in transcription, preventing transcription and hence production of enzyme protein. An antisense RNA or DNA nucleic acid molecule would hybridize to the mRNA and thus block translation of mRNA into enzyme protein.

Alternatively, a class of antisense molecules can be used to inactivate mRNA in order to decrease expression of enzyme nucleic acid. Accordingly, these molecules can treat a disorder characterized by abnormal or undesired enzyme nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the enzyme protein, such as substrate binding.

The nucleic acid molecules also provide vectors for gene therapy in patients containing cells that are aberrant in enzyme gene expression. Thus, recombinant cells, which include the patient's cells that have been engineered ex vivo and returned to the patient, are introduced into an individual where the cells produce the desired enzyme protein to treat the individual.

The invention also encompasses kits for detecting the presence of a enzyme nucleic acid in a biological sample. Experimental data as provided in FIG. 1 indicates that the enzymes of the present invention are expressed in humans in the placenta, B cells from Burkitt lymphoma, primary B-cells from tonsils detected by a virtual northern blot. In addition, PCR-based tissue screening panels indicate expression in and leukocyte. For example, the kit can comprise reagents such as a labeled or labelable nucleic acid or agent capable of detecting enzyme nucleic acid in a biological sample; means for determining the amount of enzyme nucleic acid in the sample; and means for comparing the amount of enzyme nucleic acid in the sample with a standard. The compound or agent can be packaged in a suitable container. The kit can further comprise instructions for using the kit to detect enzyme protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the enzyme proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the enzyme gene of the present invention. FIG. 3 provides information on SNPs that have been identified in a gene encoding the enzyme protein of the present invention. 41 SNP variants were found, including 7 indels (indicated by a "-") and 4 SNPs in exons, of which 2 of these cause changes in the amino acid sequence (i.e., nonsynonymous SNPs). The changes in the amino acid sequence that these SNPs cause is indicated in FIG. 3 and can readily be determined using the universal genetic code and the protein sequence provided in FIG. 2 as a reference SNPs, identified at different nucleotide positions in introns and regions 5' and 3' of the ORF, may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1 982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified enzyme gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroenzyme. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 1 70:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufinan et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual*. 2nd, ed., *Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as enzymes, appropriate secretion signals are incorporated into the vector. The signal sequence can be endogenous to the peptides or heterologous to these peptides.

Where the peptide is not secreted into the medium, which is typically the case with enzymes, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a enzyme protein or peptide that can be further purified to produce desired amounts of enzyme protein or fragments. Thus, host cells containing expression vectors are useful for peptide production.

Host cells are also useful for conducting cell-based assays involving the enzyme protein or enzyme protein fragments, such as those described above as well as other formats known in the art. Thus, a recombinant host cell expressing a native enzyme protein is useful for assaying compounds that stimulate or inhibit enzyme protein function.

Host cells are also useful for identifying enzyme protein mutants in which these functions are affected. If the mutants naturally occur and give rise to a pathology, host cells containing the mutations are useful to assay compounds that have a desired effect on the mutant enzyme protein (for example, stimulating or inhibiting function) which may not be indicated by their effect on the native enzyme protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a enzyme protein and identifying and evaluating modulators of enzyme protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the enzyme protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the enzyme protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, enzyme protein activation, and signal transduction, may not be evident from in vitro cell-free or cell-based assays. Accordingly, it is useful to provide non-human transgenic animals to assay in vivo enzyme protein function, including substrate interaction, the effect of specific mutant enzyme proteins on enzyme protein function and substrate interaction, and the effect of chimeric enzyme proteins. It is also possible to assess the effect of null mutations, that is, mutations that substantially or completely eliminate one or more enzyme protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide, wherein the amino acid sequence of said polypeptide consists of SEQ ID NO:2.

2. An isolated polypeptide, wherein the amino acid sequence of said polypeptide comprises SEQ ID NO:2.

3. A composition comprising the polypeptide of claim 1 and a carrier.

4. A composition comprising the polypeptide of claim 2 and a carrier.

* * * * *